(12) United States Patent
Wexler et al.

(10) Patent No.: US 9,095,423 B2
(45) Date of Patent: Aug. 4, 2015

(54) APPARATUS AND METHOD FOR PROVIDING FAILED-ATTEMPT FEEDBACK USING A CAMERA ON GLASSES

(71) Applicants: Yonatan Wexler, Jerusalem (IL); Amnon Shashua, Mevasseret Zion (IL)

(72) Inventors: Yonatan Wexler, Jerusalem (IL); Amnon Shashua, Mevasseret Zion (IL)

(73) Assignee: OrCam Technologies, Ltd., Jerusalem (IL)

( * ) Notice: Subject to any disclaimer, the term of this patent is extended or adjusted under 35 U.S.C. 154(b) by 0 days.

(21) Appl. No.: 14/137,033

(22) Filed: Dec. 20, 2013

(65) Prior Publication Data

US 2014/0267648 A1    Sep. 18, 2014

Related U.S. Application Data

(60) Provisional application No. 61/799,649, filed on Mar. 15, 2013, provisional application No. 61/830,122, filed on Jun. 2, 2013.

(51) Int. Cl.
H04N 9/47 (2006.01)
H04N 7/18 (2006.01)
(Continued)

(52) U.S. Cl.
CPC . *A61F 9/08* (2013.01); *G06F 3/011* (2013.01); *G06F 3/16* (2013.01); *G06F 17/2765* (2013.01); *G06K 9/00221* (2013.01); *G06K 9/00671* (2013.01); *G06K 9/74* (2013.01); *G08B 3/10* (2013.01); *G08B 6/00* (2013.01); *G09B 21/00* (2013.01); *G09B 21/001* (2013.01);
(Continued)

(58) Field of Classification Search
USPC ................. 348/61, 62, 115, 135
See application file for complete search history.

(56) References Cited

U.S. PATENT DOCUMENTS

| 6,115,482 A | 9/2000 | Sears et al. |
| 2005/0208457 A1 | 9/2005 | Fink et al. |

(Continued)

FOREIGN PATENT DOCUMENTS

| EP | 2065871 | 6/2009 |
| EP | 2 490 155 A1 | 8/2012 |

OTHER PUBLICATIONS

U.S. Appl. No. 14/136,438, filed Dec. 20, 2013, entitled "Apparatus, Method, and Computer Readable Medium for Expedited Text Reading Using Staged OCR Technique,".

(Continued)

*Primary Examiner* — Geepy Pe
(74) *Attorney, Agent, or Firm* — Finnegan, Henderson, Farabow, Garrett & Dunner LLP

(57) ABSTRACT

Apparatuses may be configured to provide feedback to a user, who may be visually-impaired. In one implementation, a method for using the apparatuses provides this feedback to a visually impaired user. The method comprises receiving from a mobile image sensor real time image data that includes a representation of an object in an environment of the visually impaired user. The mobile image sensor is configured to be connected to glasses worn by the visually impaired user. Further, the method comprises receiving a signal indicating a desire of the visually impaired user to obtain information about the object. The method also includes accessing a database holding information about a plurality of objects, and comparing information derived from the received real time image data with information in the database. The method comprises providing the visually impaired user with nonvisual feedback that the object is not locatable in the database.

23 Claims, 24 Drawing Sheets

(51) Int. Cl.
| | |
|---|---|
| H04N 7/00 | (2011.01) |
| A61F 9/08 | (2006.01) |
| G09B 21/00 | (2006.01) |
| G06K 9/00 | (2006.01) |
| H04N 5/232 | (2006.01) |
| G08B 3/10 | (2006.01) |
| G08B 6/00 | (2006.01) |
| G06F 17/27 | (2006.01) |
| G06K 9/74 | (2006.01) |
| G10L 13/04 | (2013.01) |
| G06F 3/16 | (2006.01) |
| G06F 3/01 | (2006.01) |
| H04N 5/225 | (2006.01) |
| G02C 11/00 | (2006.01) |

(52) U.S. Cl.
CPC ............ *G09B21/003* (2013.01); *G09B 21/006* (2013.01); *G10L 13/043* (2013.01); *H04N 5/2251* (2013.01); *H04N 5/2252* (2013.01); *H04N 5/23229* (2013.01); *H04N 5/23232* (2013.01); *G02C 11/10* (2013.01)

(56) References Cited

U.S. PATENT DOCUMENTS

| | | | |
|---|---|---|---|
| 2006/0017810 | A1 | 1/2006 | Kurzweil et al. |
| 2012/0075168 | A1* | 3/2012 | Osterhout et al. ............... 345/8 |
| 2012/0212593 | A1 | 8/2012 | Na'aman et al. |
| 2013/0035742 | A1 | 2/2013 | Talbot |
| 2013/0169536 | A1 | 7/2013 | Wexler et al. |
| 2013/0271584 | A1 | 10/2013 | Wexler et al. |

OTHER PUBLICATIONS

U.S. Appl. No. 14/135,727, filed Dec. 20, 2013, entitled "Systems and Method for Audible Facial Recognition,".
U.S. Appl. No. 14/137,263, filed Dec. 20, 2013, entitled "Apparatus and Method for Executing System Commands Based on Captured Image Data,".
U.S. Appl. No. 14/135,757, filed Dec. 20, 2013, entitled "Systems and Methods for Automatic Control of a Continuous Action,".
U.S. Appl. No. 14/137,373, filed Dec. 20, 2013, entitled "Apparatus and Method for Automatic Action Selection Based on Image Context,".
U.S. Appl. No. 14/135,762, filed Dec. 20, 2013, entitled "Systems and Methods for Performing a Triggered Action,".
U.S. Appl. No. 14/137,328, filed Dec. 20, 2013, entitled "Apparatus and Method for Performing Actions Based on Captured Image Data,".
U.S. Appl. No. 14/135,859, filed Dec. 20, 2013, entitled "Apparatus Connectable to Glasses,".
U.S. Appl. No. 14/137,446, filed Dec. 20, 2013, entitled "Apparatus and Method for Hierarchical Object Identification Using a Camera on Glasses,".
U.S. Appl. No. 14/135,928, filed Dec. 20, 2013, entitled "Systems and Methods for Processing Images,".
U.S. Appl. No. 14/135,775, filed Dec. 20, 2013, entitled "Systems and Methods for Providing Feedback Based on the State of an Object,".
U.S. Appl. No. 14/137,522, filed Dec. 20, 2013, entitled "Apparatus and Method for Using Background Change to Determine Context,".
U.S. Appl. No. 14/136,545, filed Dec. 20, 2013, entitled "Apparatus, Method, and Computer Readable Medium for Recognizing Text on a Curved Surface,".
U.S. Appl. No. 14/137,384, filed Dec. 20, 2013, entitled "Systems and Methods for Audibly Presenting Textual Ifnormatio Included in Image Data,".
U.S. Appl. No. 14/136,876, filed Dec. 20, 2013, entitled "Apparatus and Method for Analyzing Images.".
Karacs, Kristof et al., "Bionic Eyeglass: An Audio Guide for Visually Impaired," Biomedical Circuits and Systems Conference, 2006, BIOCAS 2006, IEEE, Piscataway, NJ, Nov. 29, 2006, p. 190-193.
Lai, Chin-Lun et al., "An Integrated Portable Vision Assistant Agency for the Visual Impaired People," 2009 IEEE International Conference on Control and Automation, Christchurch, New Zealand, Dec. 9-11, 2009 (6 pages).
Balduzzi et al., "Low-cost face bioemtry for visually impaired users," *2010 IEEE Worshop on Biometric Measurements and Sytems for Security and Medical Applications (BIOMS)*, Sep. 9, 2010, pages 45-52, IEEE, Piscataway, NJ, USA.
European Patent Office, PCT International Search Report, International Application No. PCT/IB2014/000972, Aug. 6, 2014, 4 pages.
European Patent Office, Written Opinion of the International Searching Authority, International Application No. PCT/IB2014/000972, Aug. 6, 2014, 5 pages.

\* cited by examiner

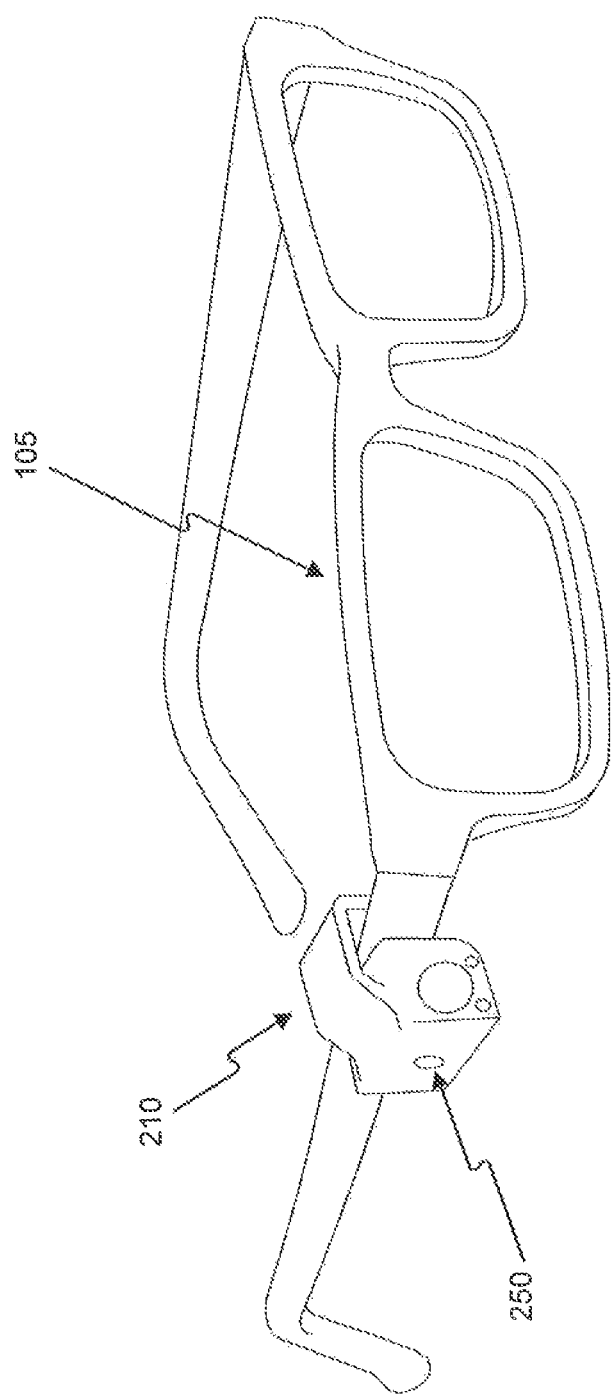

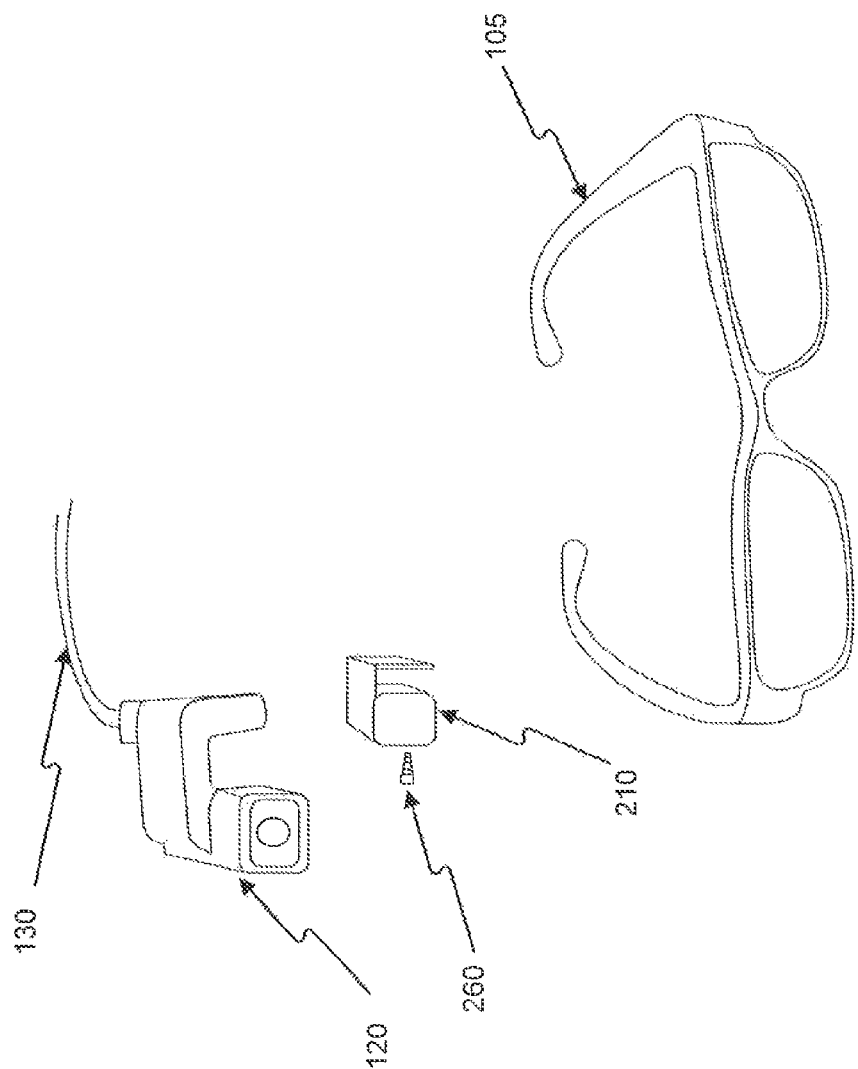

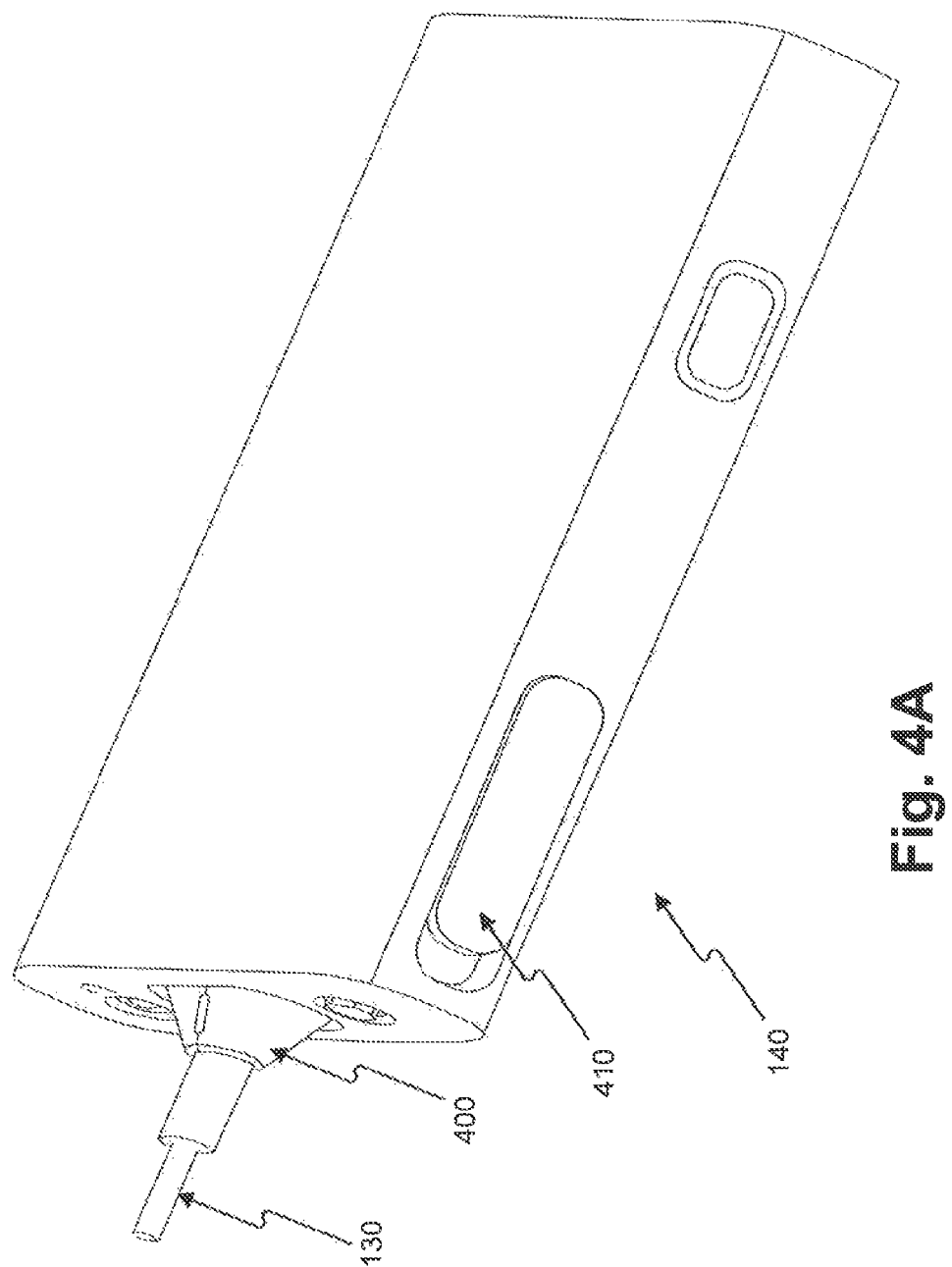

APPARATUS AND METHOD FOR PROVIDING FAILED-ATTEMPT FEEDBACK USING A CAMERA ON GLASSES

CROSS REFERENCE TO RELATED APPLICATIONS

This application claims the benefit of priority of U.S. Provisional Patent Application No. 61/799,649, filed on Mar. 15, 2013, and U.S. Provisional Patent Application No. 61/830,122, filed on Jun. 2, 2013, both of which are incorporated herein by reference in their entirety.

BACKGROUND

I. Technical Field

This disclosure generally relates to devices and methods for providing information to a user. More particularly, this disclosure relates to devices and methods for providing information to a user by processing images captured from the environment of the user.

II. Background Information

Visual acuity is an indication of the clarity or clearness of a person's vision that is commonly measured twenty feet from an object. When measuring visual acuity, the ability of a person to identify black symbols on a white background at twenty feet is compared to the ability of a person with normal eyesight. This comparison can be symbolized by a ratio. For example, a ratio of 20/70 vision means a person located at a distance of twenty feet can see what a person with normal vision can see at seventy feet. A person has low vision if he or she has a visual acuity between 20/70 and 20/200 in the better-seeing eye that cannot be corrected or improved with regular eyeglasses. The prevalence of low vision is about one in a hundred for people in their sixties and rapidly increases to one in five for people in their nineties. Low vision may also depend on the environment. For example, some individuals may be able to see only when there is ample light.

A person may have low vision (also known as visual impairment) for several reasons. Other than eye damage and failure of the brain to receive visual cues sent by the eyes, different medical conditions may cause visual impairment. Medical conditions that may cause visual impairment include Age-related Macular Degeneration (AMD), retinitis pigmentosa, cataract, and diabetic retinopathy.

AMD, which usually affects adults, is caused by damage to the retina that diminishes vision in the center of a person's visual field. The lifetime risk for developing AMD is strongly associated with certain genes. For example, the lifetime risk of developing AMD is 50% for people that have a relative with AMD, versus 12% for people that do not have relatives with AMD.

Retinitis pigmentosa is an inherited, degenerative eye disease that causes severe vision impairment and often blindness. The disease process begins with changes in pigment and damage to the small arteries and blood vessels that supply blood to the retina. There is no cure for retinitis pigmentosa and no known treatment can stop the progressive vision loss caused by the disease.

A cataract is a clouding of the lens inside the eye which leads to a decrease in vision. Over time, a yellow-brown pigment is deposited within the lens and obstructs light from passing and being focused onto the retina at the back of the eye. Biological aging is the most common cause of a cataract, but a wide variety of other risk factors (e.g., excessive tanning, diabetes, prolonged steroid use) can cause a cataract.

Diabetic retinopathy is a systemic disease that affects up to 80% of all patients who have had diabetes for ten years or more. Diabetic retinopathy causes microvascular damage to a blood-retinal barrier in the eye and makes the retinal blood vessels more permeable to fluids.

People with low vision experience difficulties due to lack of visual acuity, field-of-view, color perception, and other visual impairments. These difficulties affect many aspects of everyday life. Persons with low vision may use magnifying glasses to compensate for some aspects of low vision. For example, if the smallest letter a person with 20/100 vision can read is five times larger than the smallest letter that a person with 20/20 vision can read, then 5× magnification should make everything that is resolvable to the person with 20/20 vision resolvable to the person with low vision. However, magnifying glasses are expensive and cannot remedy all aspects of low vision. For example, a person with low vision who wears magnifying glasses may still have a difficult time recognizing details from a distance (e.g., people, signboards, traffic lights, etc.). Accordingly, there is a need for other technologies that can assist people who have low vision accomplish everyday activities.

SUMMARY

Embodiments consistent with the present disclosure provide devices and methods for providing information to a user by processing images captured from the environment of the user. The disclosed embodiments may assist persons who have low vision.

In accordance with a disclosed embodiment, an apparatus is provided for providing feedback to a visually impaired user. The apparatus may comprise a mobile image sensor configured to capture real time image data from an environment of the user, a mobile power source for powering at least the image sensor, and at least one mobile processor device. The mobile processor device may be configured to receive from the mobile image sensor real time image data that includes a representation of an object in the environment of the user. Further, the mobile processor device may be configured to receive a signal indicating a desire of the user to obtain information about the object. Also, the mobile processor device may be configured to access a database holding information about a plurality of objects, and to compare information derived from the received real time image data with information in the database. The mobile processor device may be further configured to provide the user with nonvisual feedback indicating that the information about the object is not locatable in the database.

In accordance with a disclosed embodiment, an apparatus is provided for providing feedback to a user. The apparatus may comprise a mobile image sensor configured to be connected to glasses worn by the user to capture real time image data that substantially coincides with a field of view of the user, a mobile power source for powering at least the image sensor, and at least one mobile processor device. The mobile processor device may be configured to receive from the mobile image sensor real time image data that includes a representation of an object in the environment of the user. Further, the mobile processor device may be configured to identify a trigger in the image data, wherein the trigger is associated with the user's desire to obtain information about the object. Also, the mobile processor device may be configured to process the representation of the object to retrieve information. The mobile processor device may be further configured to provide the user with nonvisual feedback indicating that the information about the object was not retrieved.

In accordance with a disclosed embodiment, a method is provided for providing feedback to a visually impaired user. The method comprises receiving from a mobile image sensor real time image data that includes a representation of an object in an environment of the visually impaired user. The mobile image sensor is configured to be connected to glasses worn by the visually impaired user. Further, the method comprises receiving a signal indicating a desire of the visually impaired user to obtain information about the object. The method also includes accessing a database holding information about a plurality of objects, and comparing information derived from the received real time image data with information in the database. The method comprises providing the visually impaired user with nonvisual feedback that the object is not locatable in the database.

Consistent with other disclosed embodiments, non-transitory computer-readable storage media may store program instructions, which are executed by at least one processor device and perform any of the methods described herein.

The foregoing general description and the following detailed description are exemplary and explanatory only and are not restrictive of the claims.

BRIEF DESCRIPTION OF THE DRAWINGS

The accompanying drawings, which are incorporated in and constitute a part of this disclosure, illustrate various disclosed embodiments. In the drawings:

FIG. 2C is a schematic illustration of the support shown in FIG. 2A mounted on a pair of glasses;

FIG. 2E is an exploded view of FIG. 2D;

FIG. 4A is a schematic illustration of an example of a processing unit from a first viewpoint;

DETAILED DESCRIPTION

Figure 1:
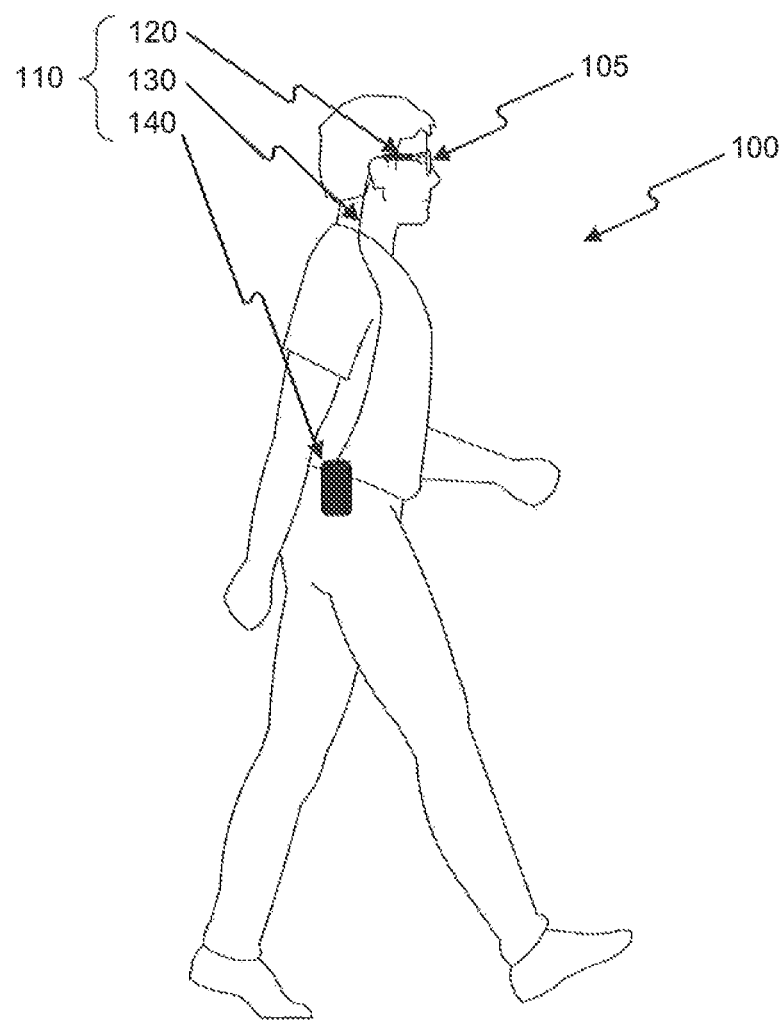
FIG. 1 is a schematic illustration of a user wearing an apparatus for aiding persons who have low vision.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Disclosed embodiments provide devices and methods for assisting people who have low vision. One example of the disclosed embodiments is a device that includes a camera configured to capture real-time image data from the environment of the user. The device also includes a processing unit configured to process the real-time image data and provide real-time feedback to the user. The real-time feedback may include, for example, an output that audibly identifies individuals from a distance, reads signboards, and/or identifies the state of a traffic light.

FIG. 1 illustrates a user 100 wearing an apparatus 110 connected to glasses 105, consistent with a disclosed embodiment. Apparatus 110 may provide functionality for aiding user 100 with various daily activities that are otherwise difficult for user 100 to accomplish due to low vision. Glasses 105 may be prescription glasses, magnifying glasses, non-prescription glasses, safety glasses, sunglasses, etc.

As shown in FIG. 1, apparatus 110 includes a sensory unit 120 and a processing unit 140. Sensory unit 120 may be connected to a support (not shown in FIG. 1) that is mounted on glasses 105. In addition, sensory unit 120 may include an image sensor (not shown in FIG. 1) for capturing real-time image data of the field-of-view of user 100. The term "image data" includes any form of data retrieved from optical signals in the near-infrared, infrared, visible, and ultraviolet spectrums. The image data may be used to form video clips and/or photographs.

Processing unit 140 may communicate wirelessly or via a wire 130 connected to sensory unit 120. In some embodiments, processing unit 140 may produce an output of audible feedback to user 100 (e.g., using a speaker or a bone conduction headphone).

Apparatus 110 is one example of a device capable of implementing the functionality of the disclosed embodiments. Other devices capable of implementing the disclosed embodiments include, for example, a mobile computer with a camera (e.g., a smartphone, a smartwatch, a tablet, etc.) or a clip-on-camera configured to communicate with a processing unit (e.g., a smartphone or a dedicated processing unit, which can be carried in a pocket). A person skilled in the art will appreciate that different types of devices and arrangements of devices may implement the functionality of the disclosed embodiments.

Figure 2A:
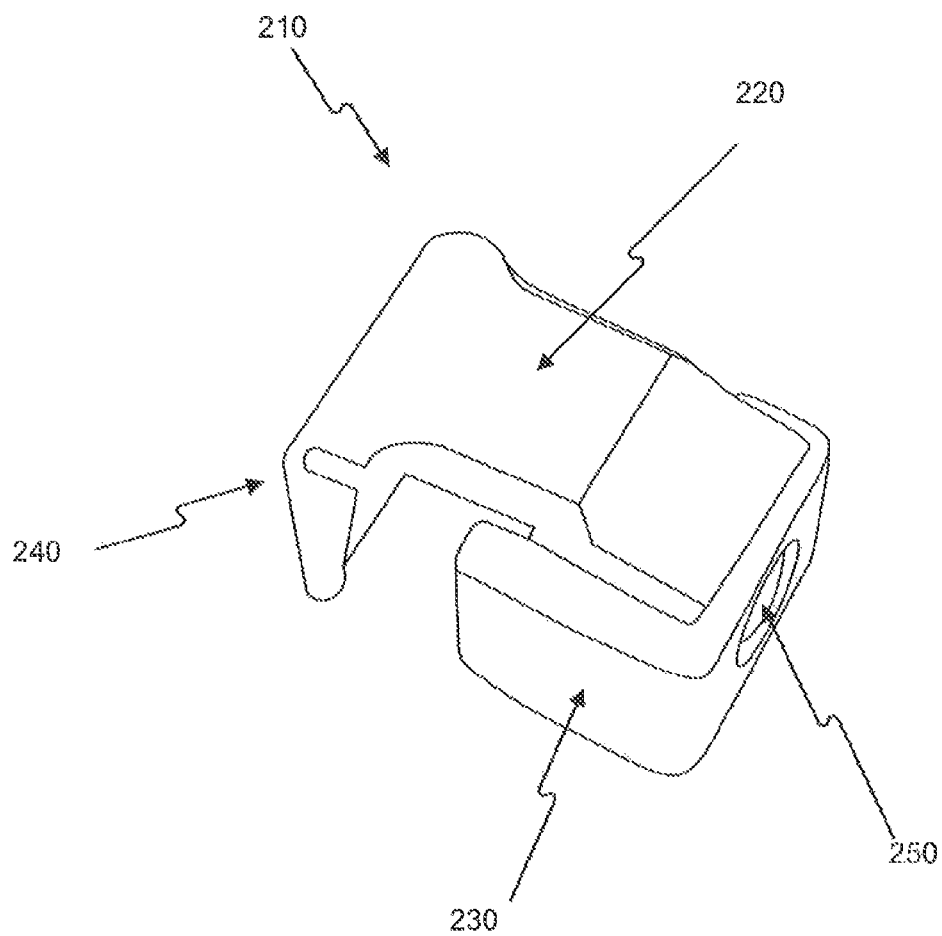
FIG. 2A is a schematic illustration of an example of a support from a first viewpoint.

FIG. 2A is a schematic illustration of an example of a support 210. As discussed in connection with FIG. 1, support 210 may be mounted on glasses 105 and connect to sensory unit 120. The term "support" includes any device or structure that enables detaching and reattaching of a device including a camera to a pair of glasses or to another object (e.g., a helmet). Support 210 may be made from plastic (e.g., polycarbonate), metal (e.g., aluminum), or a combination of plastic and metal (e.g., carbon fiber graphite). Support 210 may be mounted on glasses 105 using screws, bolts, snaps, or any fastening means used in the art.

As shown in FIG. 2A, support 210 includes a base 230 connected to a clamp 240. A bridge 220 connects base 230 with clamp 240. Base 230 and clamp 240 enable sensory unit 120 to easily attach to and detach from support 210. In one embodiment, base 230 may include an internally threaded member 250 for cooperating with a screw (not shown in FIG. 2A) to mount support 210 on glasses 105.

Figure 2B:
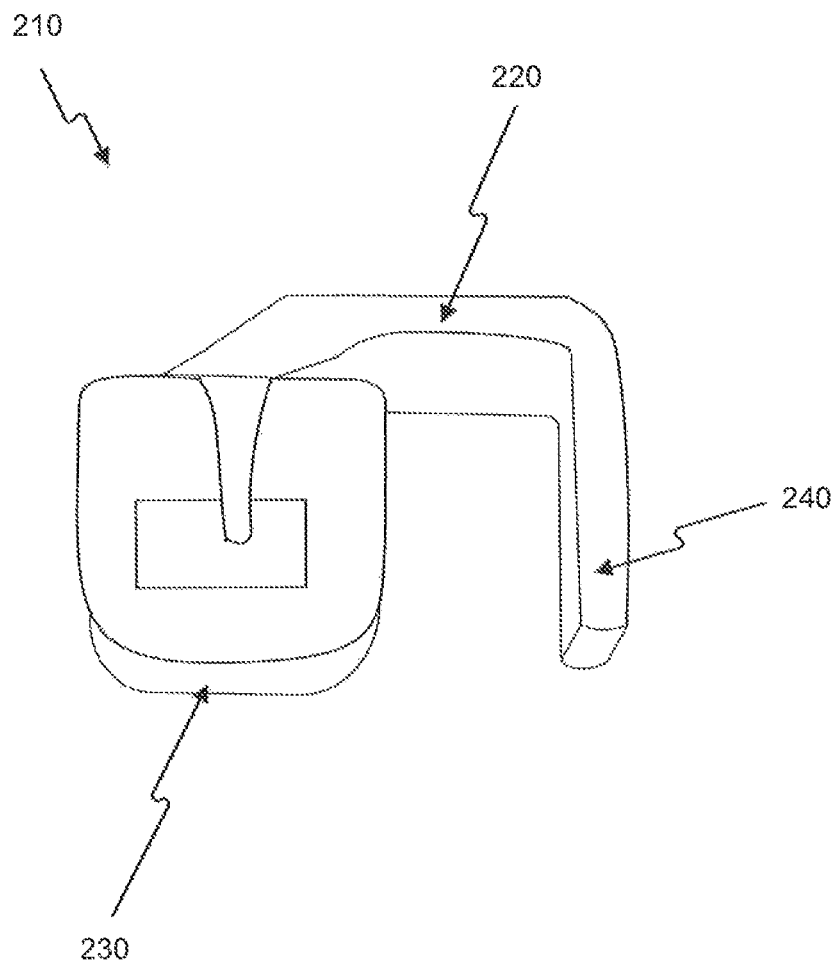
FIG. 2B is a schematic illustration of the support shown in FIG. 2A from a second viewpoint.

FIG. 2B illustrates support 210 from a second viewpoint. The viewpoint shown in FIG. 2B is from a side orientation of support 210.

FIG. 2C illustrates support 210 mounted on glasses 105. Support 210 may be configured for mounting on any kind of glasses (e.g., eyeglasses, sunglasses, 3D glasses, safety glasses, etc.). As shown in FIG. 2C, sensory unit 120 is not attached to support 210 and, accordingly, support 210 may be sold separately from apparatus 110. This arrangement makes apparatus 110 compatible with a variety of glasses. For example, some users may have several pairs of glasses and may wish to mount a support on each pair of glasses.

In other embodiments, support 210 may be an integral part of a pair of glasses, or sold and installed by an optometrist. For example, support 210 may be configured for mounting on the arms of glasses 105 near the frame front, but before the hinge. Alternatively, support 210 may be configured for mounting on the bridge of glasses 105.

Figure 2D:
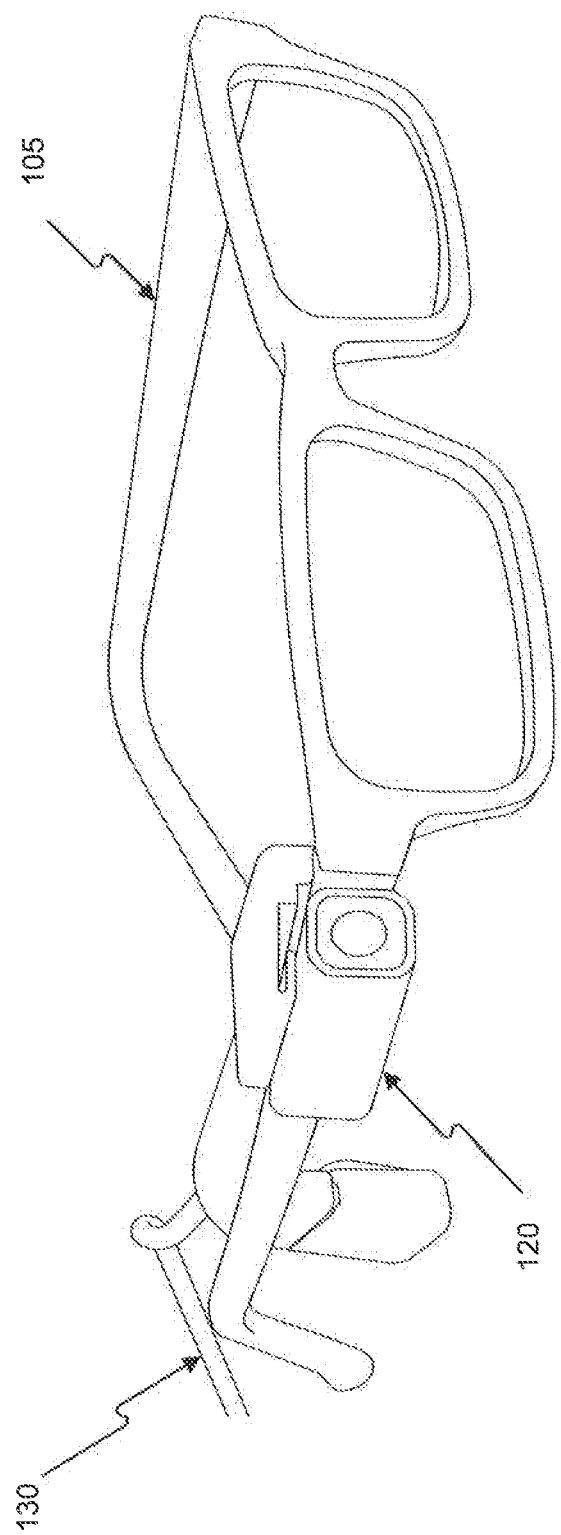
FIG. 2D is a schematic illustration of a sensory unit attached to the support that is mounted on the pair of glasses shown in FIG. 2C.

FIG. 2D illustrates sensory unit 120 attached to support 210 (not visible in FIG. 2D), and support 210 mounted on glasses 105. In some embodiments, support 210 may include a quick release mechanism for disengaging and reengaging sensory unit 120. For example, support 210 and sensory unit 120 may include magnetic elements. As an alternative example, support 210 may include a male latch member and sensory unit 120 may include a female receptacle.

When sensory unit 120 is attached (or reattached) to support 210, the field-of-view of a camera associated with sensory unit 120 may be substantially identical to the field-of-view of user 100. Accordingly, in some embodiments, after support 210 is attached to sensory unit 120, directional calibration of sensory unit 120 may not be required because sensory unit 120 aligns with the field-of-view of user 100.

In other embodiments, support 210 may include an adjustment component (not shown in FIG. 2D) to enable calibration of the aiming direction of sensory unit 120 in a substantially set position that is customized to user 100 wearing glasses 105. For example, the adjustment component may include an adjustable hinge to enable vertical and horizontal alignment of the aiming direction of sensory unit 120. Adjusting the alignment of sensory unit 120 may assist users who have a unique and individual visual impairment. The adjustment may be internal or external to sensory unit 120.

FIG. 2E is an exploded view of the components shown in FIG. 2D. Sensory unit 120 may be attached to glasses 105 in the following way. Initially, support 210 may be mounted on glasses 105 using screw 260. Next, screw 260 may be inserted into internally threaded member 250 (not shown in FIG. 2E) in the side of support 210. Sensory unit 120 may then be clipped on support 210 such that it is aligned with the field-of-view of user 100.

Figure 3A:
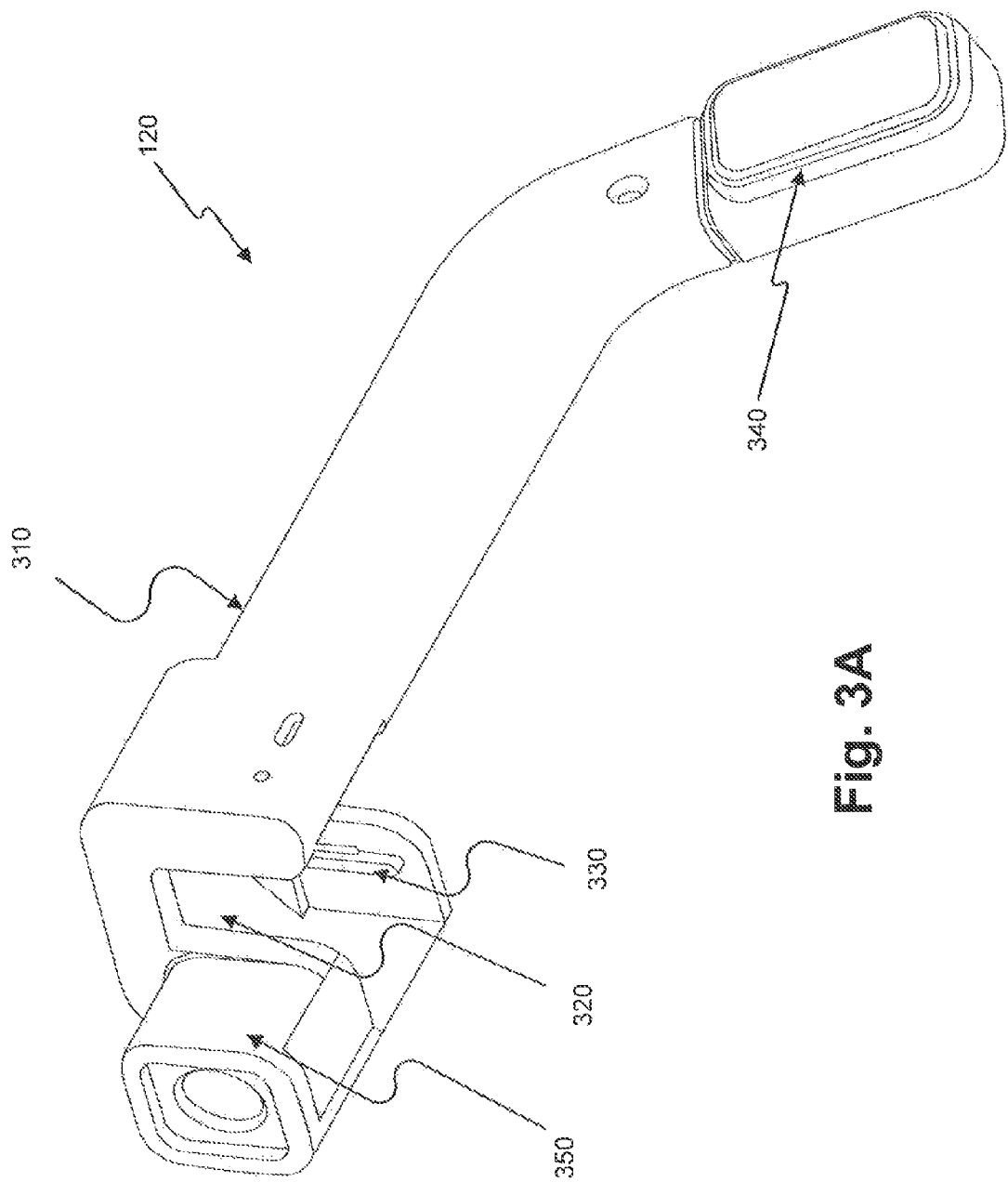
FIG. 3A is a schematic illustration of an example of a sensory unit from a first viewpoint.

FIG. 3A is a schematic illustration of sensory unit 120 from a first viewpoint. As shown in FIG. 3A, sensory unit 120 includes a feedback-outputting unit 340 and an image sensor 350.

Sensory unit 120 is configured to cooperate with support 210 using clip 330 and groove 320, which fits the dimensions of support 210. The term "sensory unit" refers to any electronic device configured to capture real-time images and provide a non-visual output. Furthermore, as discussed above, sensory unit 120 includes feedback-outputting unit 340. The term "feedback-outputting unit" includes any device configured to provide information to a user.

In some embodiments, feedback-outputting unit 340 may be configured to be used by blind persons and persons with low vision. Accordingly, feedback-outputting unit 340 may be configured to output nonvisual feedback. The term "feedback" refers to any output or information provided in response to processing at least one image in an environment. For example, feedback may include a descriptor of a branded product, an audible tone, a tactile response, and/or information previously recorded by user 100. Furthermore, feedback-outputting unit 340 may comprise appropriate components for outputting acoustical and tactile feedback that people with low vision can interpret. For example, feedback-outputting unit 340 may comprise audio headphones, a speaker, a bone conduction headphone, interfaces that provide tactile cues, vibrotactile stimulators, etc.

As discussed above, sensory unit 120 includes image sensor 350. The term "image sensor" refers to a device capable of detecting and converting optical signals in the near-infrared, infrared, visible, and ultraviolet spectrums into electrical signals. The electric signals may be used to form an image based on the detected signal. For example, image sensor 350 may be part of a camera. In some embodiments, when sensory unit 120 is attached to support 210, image sensor 350 may acquire a set aiming direction without the need for directional calibration. The set aiming direction of image sensor 350 may substantially coincide with the field-of-view of user 100 wearing glasses 105. For example, a camera associated with image sensor 350 may be installed within sensory unit 120 in a predetermined angle in a position facing slightly downwards (e.g., 5-15 degrees from the horizon). Accordingly, the set aiming direction of image sensor 350 may match the field-of-view of user 100.

As shown in FIG. 3A, feedback-outputting unit 340 and image sensor 350 are included in a housing 310. The term "housing" refers to any structure that at least partially covers, protects, or encloses a sensory unit. The housing may be made from one or more different materials (e.g., plastic or aluminum). In one embodiment, housing 310 may be designed to engage with a specific pair of glasses having a specific support (e.g., support 210). In an alternative embodiment, housing 310 may be designed to engage more than one pair of glasses, each having a support (e.g., support 210) mounted thereon. Housing 310 may include a connector for receiving power from an external mobile-power-source or an internal mobile-power-source, and for providing an electrical connection to image sensor 350.

Figure 3B:
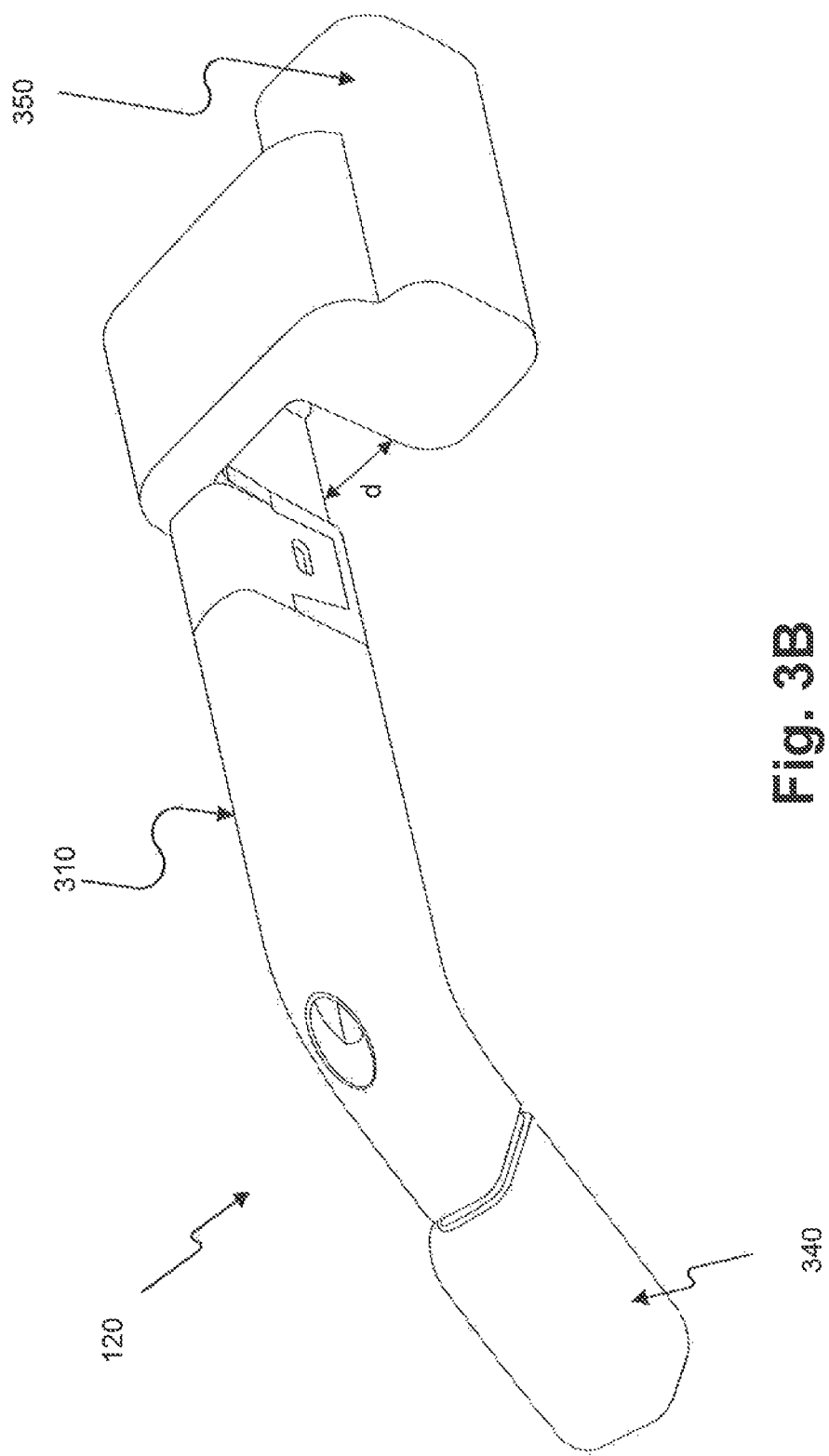
FIG. 3B is a schematic illustration of the sensory unit shown in FIG. 3A from a second viewpoint.

FIG. 3B is a schematic illustration of sensory unit 120 from a second viewpoint. As shown in FIG. 3B, housing 310 includes a U-shaped element. An inner distance "d" between each side of the U-shaped element is larger than the width of the arm of glasses 105. Additionally, the inner distance "d" between each side of the U-shaped element is substantially equal to a width of support 210. The inner distance "d" between each side of the U-shaped element may allow user 100 to easily attach housing 310 to support 210, which may be mounted on glasses 105. As illustrated in FIG. 3B, image sensor 350 is located on one side of the U-shaped element and feedback-outputting unit 340 is located on another side of the U-shaped element.

Figure 3C:
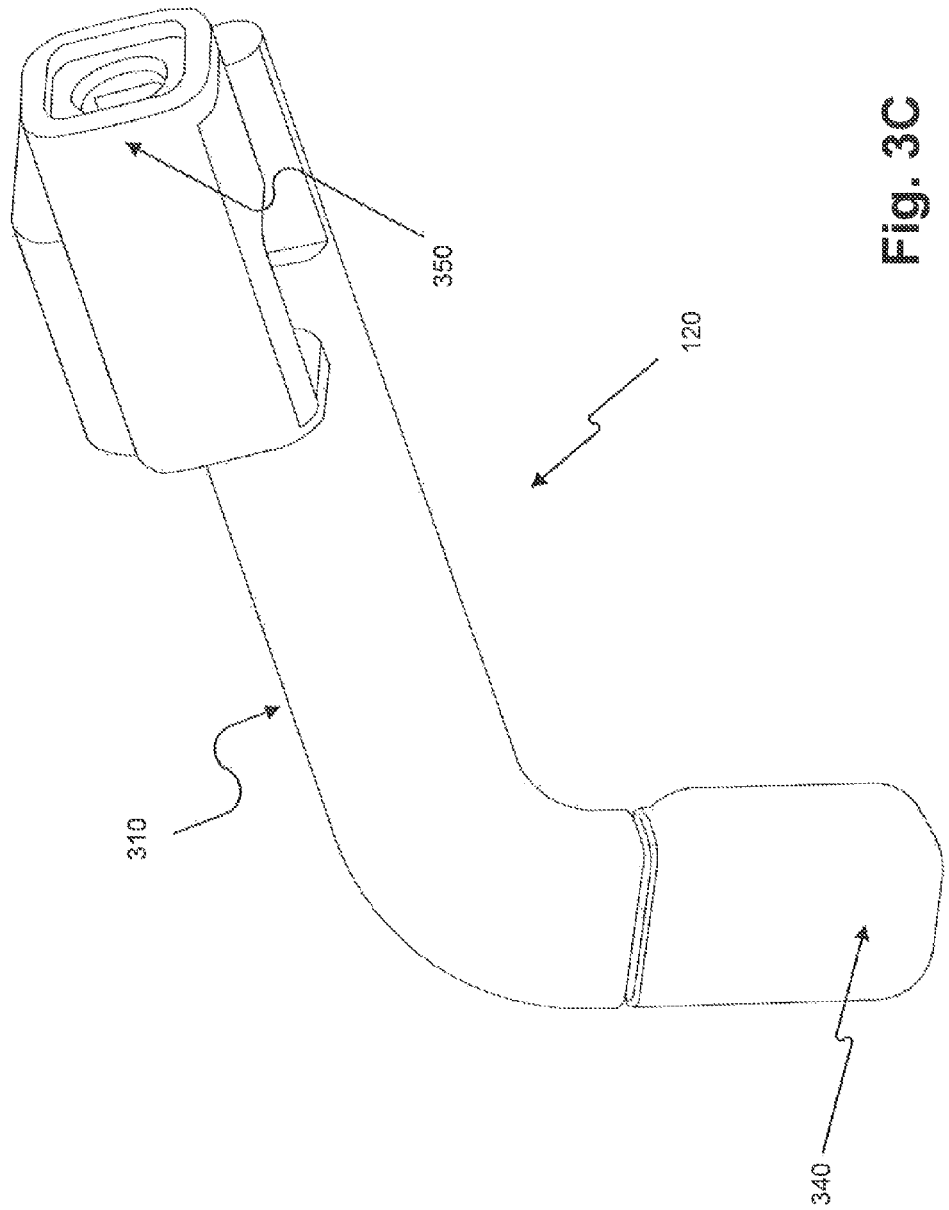
FIG. 3C is a schematic illustration of the sensory unit shown in FIG. 3A from a third viewpoint.

FIG. 3C is a schematic illustration of sensory unit 120 from a third viewpoint. The viewpoint shown in FIG. 3C is from a side orientation of sensory unit 120 and shows the side of the U-shaped element that includes image sensor 350.

Figure 3D:
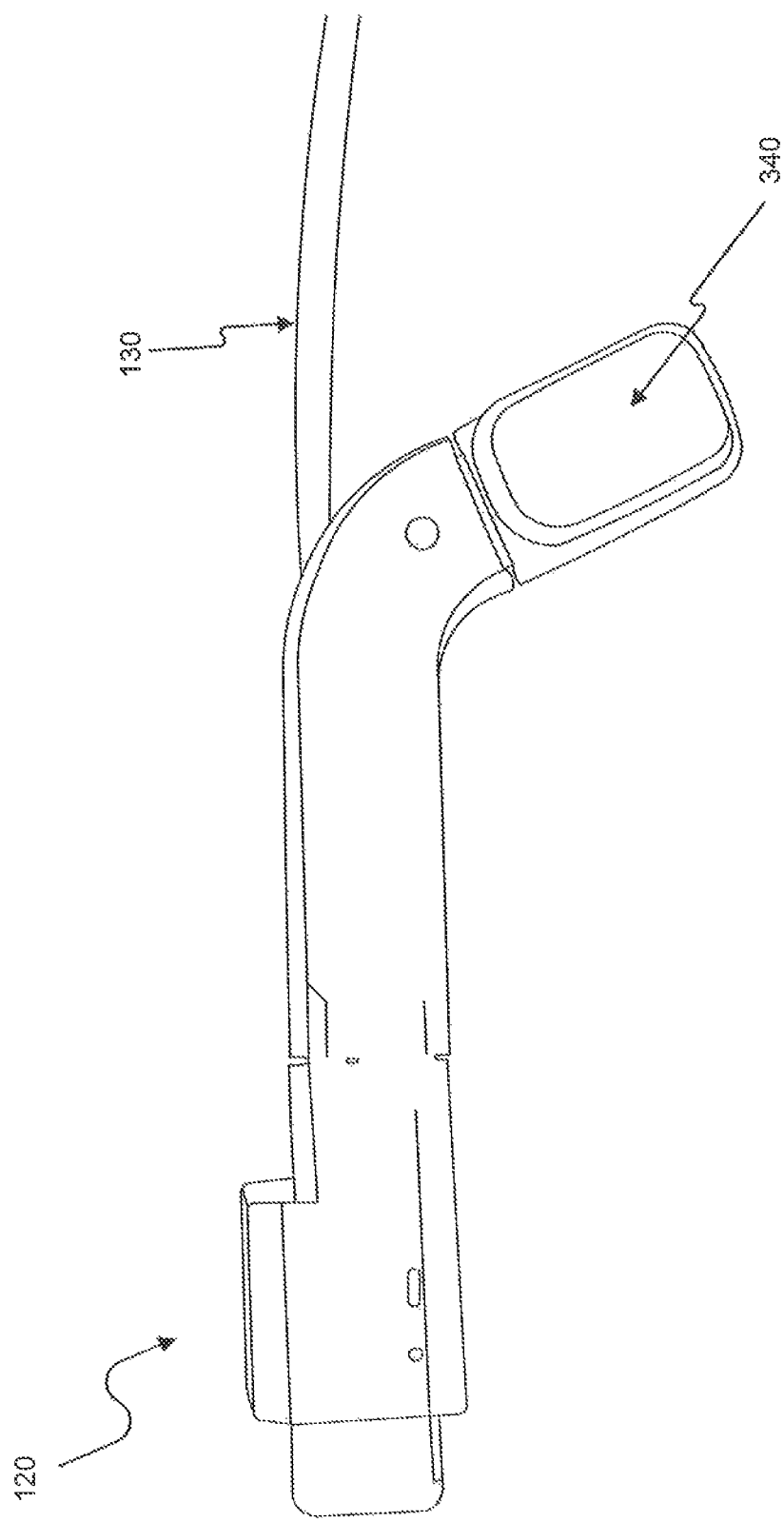
FIG. 3D is a schematic illustration of the sensory unit shown in FIG. 3A from a fourth viewpoint.

FIG. 3D is a schematic illustration of sensory unit 120 from a fourth viewpoint. The viewpoint shown in FIG. 3D is from an opposite side of the orientation shown in FIG. 3C. FIG. 3D shows the side of the U-shaped element that includes feedback-outputting unit 340.

Figure 3E:
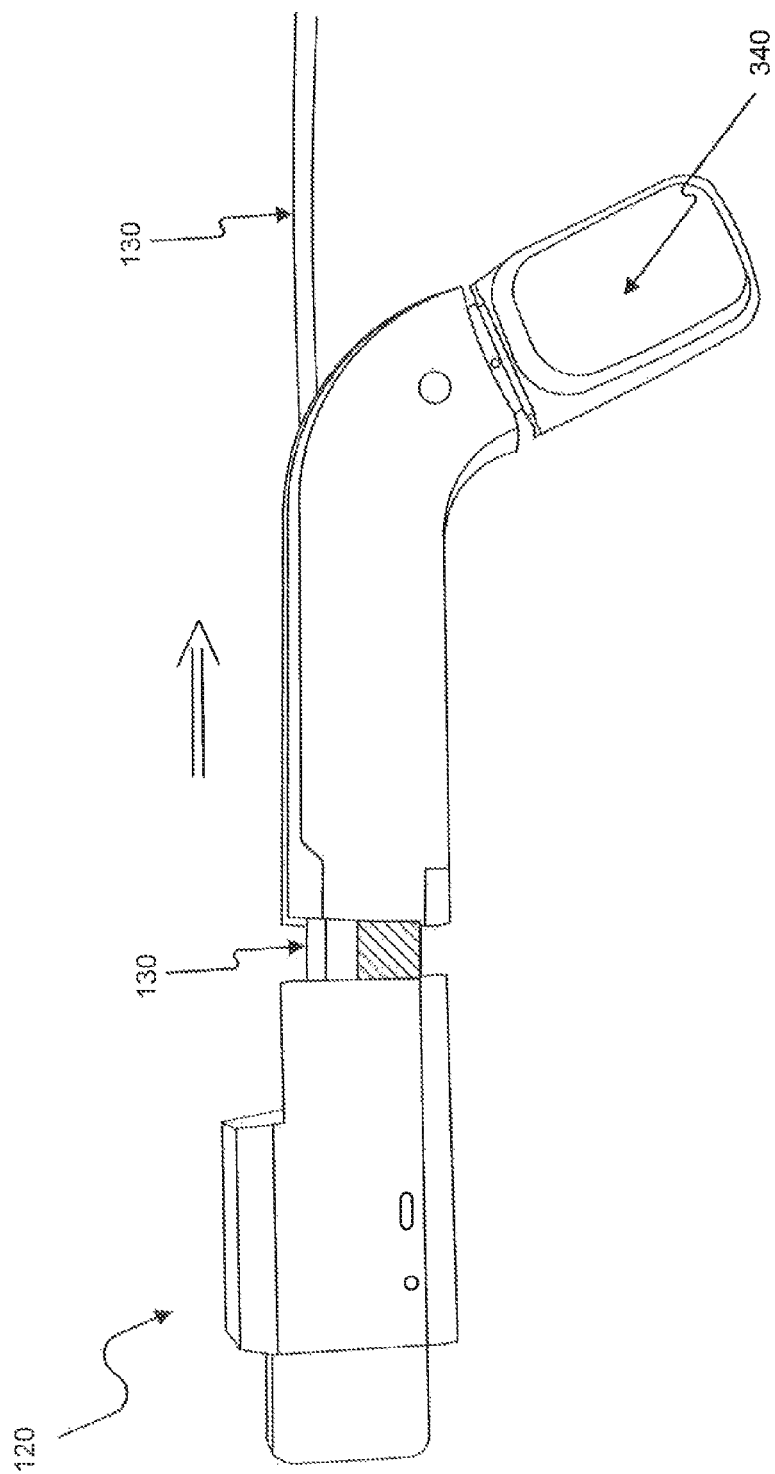
FIG. 3E is a schematic illustration of the sensory unit shown in FIG. 3A in an extended position.

FIG. 3E is a schematic illustration of the sensory unit shown in FIG. 3A in an extended position. As shown in FIG. 3E, a portion of sensory unit 120 is extendable and wire 130 may pass through a channel of sensory unit 120. This arrangement may allow a user to adjust the length and the angle of sensory unit 120 without interfering with the operation of apparatus 110.

User 100 may adjust the U-shaped element of sensory unit 120 so that feedback-outputting unit 340 is positioned adjacent to the user's ear or the user's temple. Accordingly, sensory unit 120 may be adjusted for use with different users who may have different head sizes. Alternatively, a portion of sensory unit 120 may be flexible such that the angle of feedback-outputting unit 340 is relative to the user's ear or the user's temple.

FIG. 4A is a schematic illustration of processing unit 140. As shown in FIG. 4A, processing unit 140 has a rectangular shape, which easily fits in a pocket of user 100. Processing unit 140 includes a connector 400 for connecting wire 130 to processing unit 140. Wire 130 may be used to transmit power from processing unit 140 to sensory unit 120, and data to and from processing unit 140 to sensory unit 120. Alternatively, wire 130 may comprise multiple wires (e.g., a wire dedicated to power transmission and a wire dedicated to data transmission).

Processing unit 140 includes a function button 410 for enabling user 100 to provide input to apparatus 110. Function button 410 may accept different types of tactile input (e.g., a tap, a click, a double-click, a long press, a right-to-left slide, a left-to-right slide). In some embodiments, each type of input may be associated with a different action. For example, a tap may be associated with the function of confirming an action, while a right-to-left slide may be associated with the function of repeating the last output.

Figure 4B:
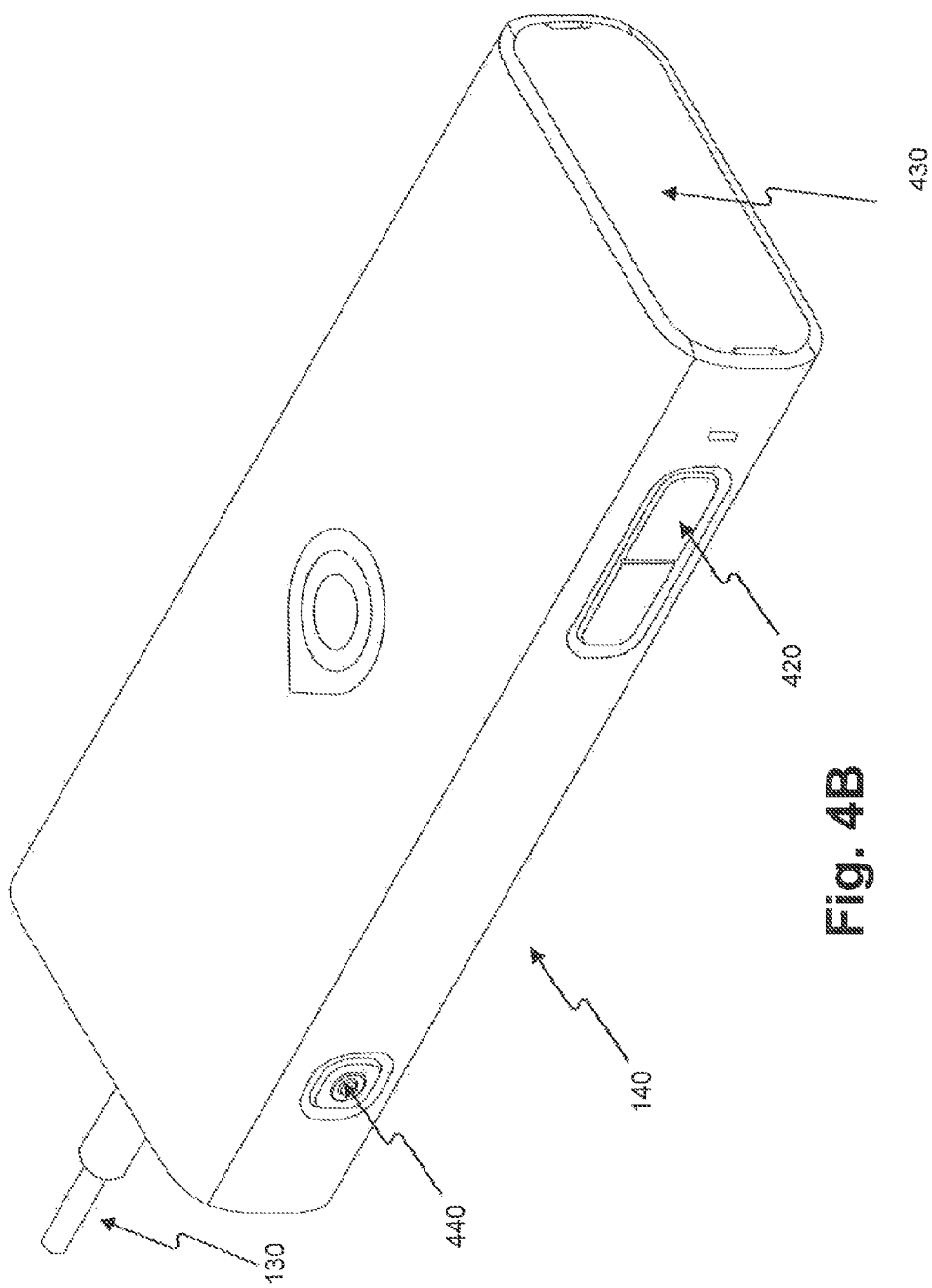
FIG. 4B is a schematic illustration of the processing unit shown in FIG. 4A from a second viewpoint.

FIG. 4B is a schematic illustration of processing unit 140 from a second viewpoint. As shown in FIG. 4B, processing unit 140 includes a volume switch 420, a battery pack compartment 430, and a power port 440. In one embodiment, user 100 may charge apparatus 110 using a charger connectable to power port 440. Alternatively, user 100 may replace a battery pack (not shown) stored in battery pack compartment 430.

Figure 5A:
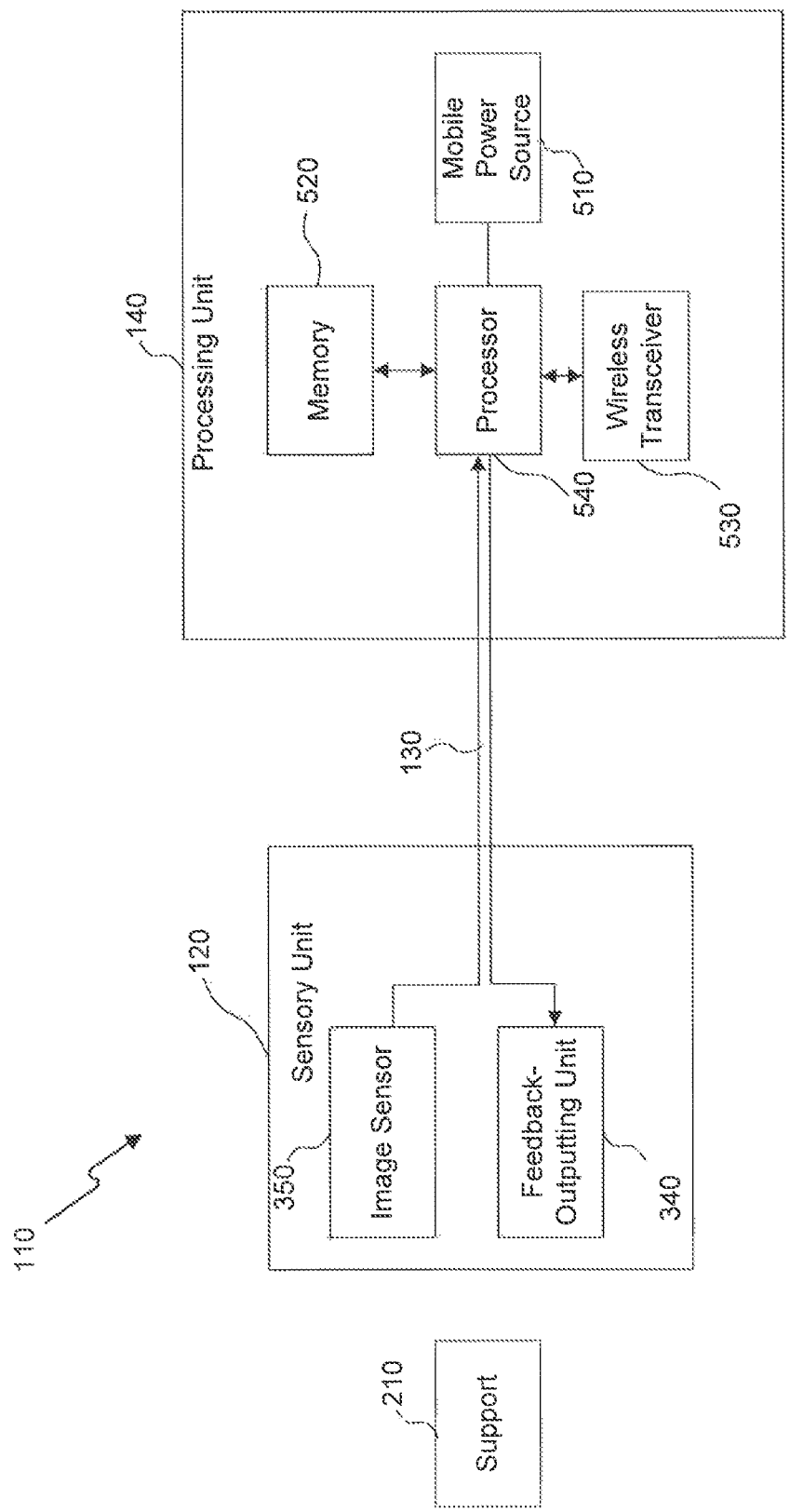
FIG. 5A is a block diagram illustrating an example of the components of an apparatus for aiding persons who have low vision according to a first embodiment.

FIG. 5A is a block diagram illustrating the components of apparatus 110 according to a first embodiment. Specifically, FIG. 5A depicts an embodiment in which apparatus 110 comprises sensory unit 120 and processing unit 140, as discussed in connection with, for example, FIG. 1. Furthermore, sensory unit 120 may be physically coupled to support 210.

As shown in FIG. 5A, sensory unit 120 includes feedback-outputting unit 340 and image sensor 350. Although one image sensor is depicted in FIG. 5A, sensory unit 120 may include a plurality of image sensors (e.g., two image sensors). For example, in an arrangement with more than one image sensor, each of the image sensors may be face a different direction or be associated with a different camera (e.g., a wide angle camera, a narrow angle camera, an IR camera, etc.). In other embodiments (not shown in the figure) sensory unit 120 may also include buttons and other sensors such as a microphone and inertial measurements devices.

As further shown in FIG. 5A, sensory unit 120 is connected to processing unit 140 via wire 130. Processing unit 140 includes a mobile power source 510, a memory 520, a wireless transceiver 530, and a processor 540.

Processor 540 may constitute any physical device having an electric circuit that performs a logic operation on input or inputs. For example, processor 540 may include one or more integrated circuits, microchips, microcontrollers, microprocessors, all or part of a central processing unit (CPU), graphics processing unit (GPU), digital signal processor (DSP), field-programmable gate array (FPGA), or other circuits suitable for executing instructions or performing logic operations. The instructions executed by processor 540 may, for example, be pre-loaded into a memory integrated with or embedded into processor 540 or may be stored in a separate memory (e.g., memory 520). Memory 520 may comprise a Random Access Memory (RAM), a Read-Only Memory (ROM), a hard disk, an optical disk, a magnetic medium, a flash memory, other permanent, fixed, or volatile memory, or any other mechanism capable of storing instructions.

Although one processor is shown in FIG. 5A, processing unit 140 may include more than one processor. Each processor may have a similar construction or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically or by other means that permit them to interact.

In some embodiments, processor 540 may change the aiming direction of image sensor 350 using image data provided from image sensor 350. For example, processor 540 may recognize that a user is reading a book and determine that the aiming direction of image sensor 350 is offset from the text. That is, because the words in the beginning of each line of text are not fully in view, processor 540 may determine that image sensor 350 is tilted down and to the right. Responsive thereto, processor 540 may adjust the aiming direction of image sensor 350.

Processor 540 may access memory 520. Memory 520 may be configured to store information specific to user 100. For example, data for image representations of known individuals, favorite products, personal items, etc., may be stored in memory 520. In one embodiment, user 100 may have more than one pair of glasses, with each pair of glasses having support 210 mounted thereon. Accordingly, memory 520 may store information (e.g., personal settings) associated with each pair of glasses. For example, when a user wears his sunglasses may have different preferences than when the user wears reading glasses.

As shown in FIG. 5A, processing unit 140 includes mobile power source 510. Mobile power source 510 may be configured to power processing unit 140 and/or sensory unit 120. The term "mobile power source" includes any device capable of providing electrical power, which can be easily carried by a hand (e.g., the total weight of mobile power source 510 may be less than a pound). Thus, the mobility of the power source enables user 100 to use apparatus 110 in a variety of situations. For example, mobile power source 510 may include one or more batteries (e.g., nickel-cadmium batteries, nickel-metal hydride batteries, and lithium-ion batteries) or any other type of electrical power supply. In some embodiments, mobile power source 510 may be rechargeable and contained within a casing that holds processing unit 140. In other embodiments, mobile power source 510 may include one or more energy harvesting devices for converting ambient energy into electrical energy (e.g., portable solar power units, human vibration units, etc.).

Apparatus 110 may operate in a low-power-consumption mode and in a processing-power-consumption mode. For example, mobile power source 510 can produce five hours of processing-power-consumption mode and fifteen hours of low-power-consumption mode. Accordingly, different power consumption modes may allow mobile power source 510 to produce sufficient power for powering processing unit 140 for various time periods (e.g., more than two hours, more than four hours, more than ten hours, etc.).

Mobile power source 510 may power one or more wireless transceivers (e.g., wireless transceiver 530 in FIG. 5A). The term "wireless transceiver" refers to any device configured to exchange transmissions over an air interface by use of radio frequency, infrared frequency, magnetic field, or electric field. Wireless transceiver 530 may use any known standard to transmit and/or receive data (e.g., Wi-Fi, Bluetooth®, Bluetooth Smart, 802.15.4, or ZigBee). In some embodiments, wireless transceiver 530 may transmit data (e.g., raw image data or audio data) from image sensor 350 to processing unit 140, or wireless transceiver 530 may transmit data from processing unit 140 to feedback-outputting unit 340.

In another embodiment, wireless transceiver 530 may communicate with a different device (e.g., a hearing aid, the user's smartphone, or any wirelessly controlled device) in the environment of user 100. For example, wireless transceiver 530 may communicate with an elevator using a Bluetooth® controller. In such an arrangement, apparatus 110 may recognize that user 100 is approaching an elevator and call the elevator, thereby minimizing wait time. In another example, wireless transceiver 530 may communicate with a smart TV. In such an arrangement, apparatus 110 may recognize that user 100 is watching television and identify specific hand movements as commands for the smart TV (e.g., switching channels). In yet another example, wireless transceiver 530 may communicate with a virtual cane. A virtual cane is any device that uses a laser beam or ultrasound waves to determine the distance from user 100 to an object.

Figure 5B:
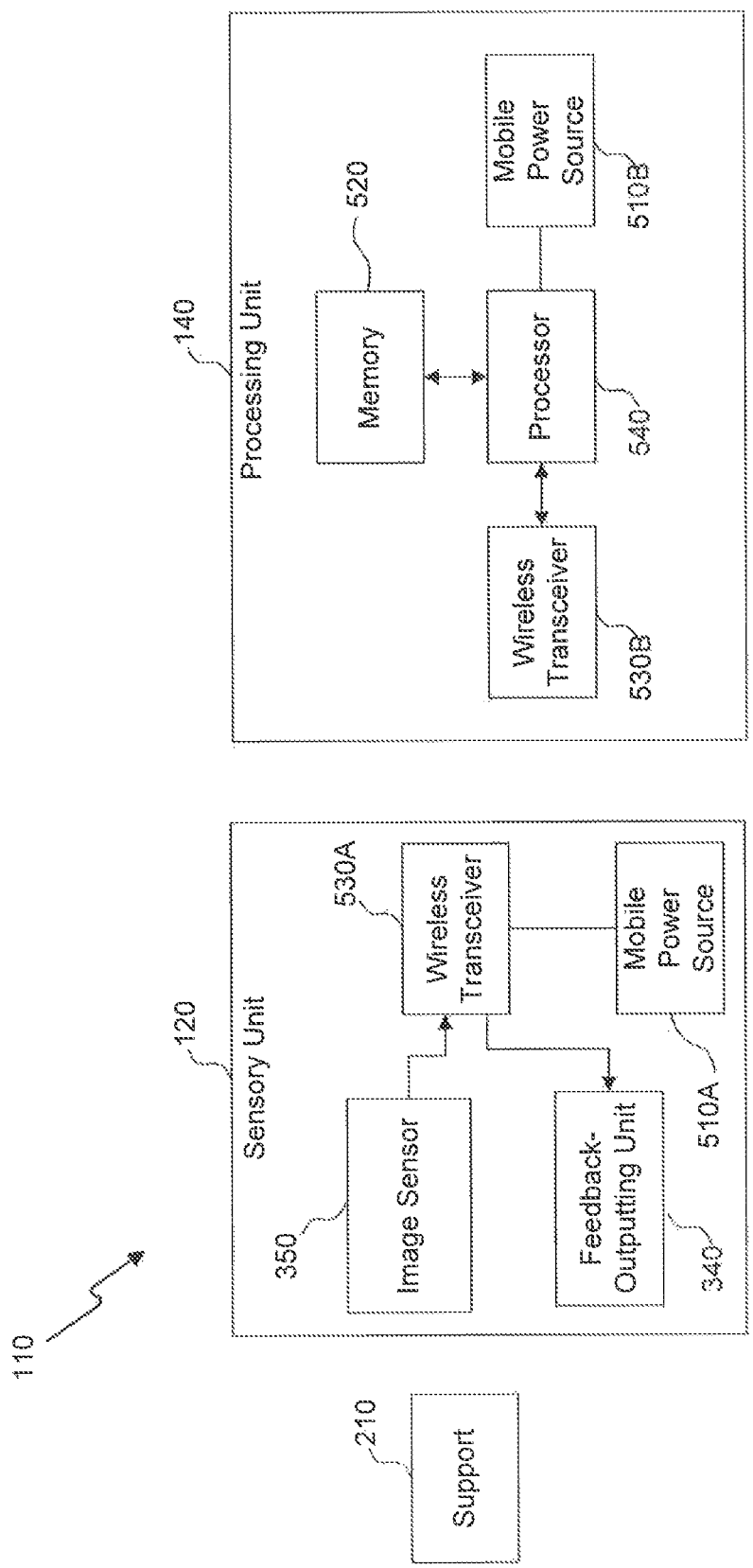
FIG. 5B is a block diagram illustrating an example of the components of an apparatus for aiding persons who have low vision according to a second embodiment.

FIG. 5B is a block diagram illustrating the components of apparatus 110 according to a second embodiment. In FIG. 5B, similar to the arrangement shown in FIG. 5A, support 210 is used to couple sensory unit 120 to a pair of glasses. However, in the embodiment shown in FIG. 5B, sensory unit 120 and processing unit 140 communicate wirelessly. For example, wireless transceiver 530A can transmit image data to processing unit 140 and receive information to be outputted via feedback-outputting unit 340.

In this embodiment, sensory unit 120 includes feedback-outputting unit 340, mobile power source 510A, wireless transceiver 530A, and image sensor 350. Mobile power source 510A is contained within sensory unit 120. As further shown in FIG. 5B, processing unit 140 includes wireless transceiver 530B, processor 540, mobile power source 510B, and memory 520.

Figure 5C:
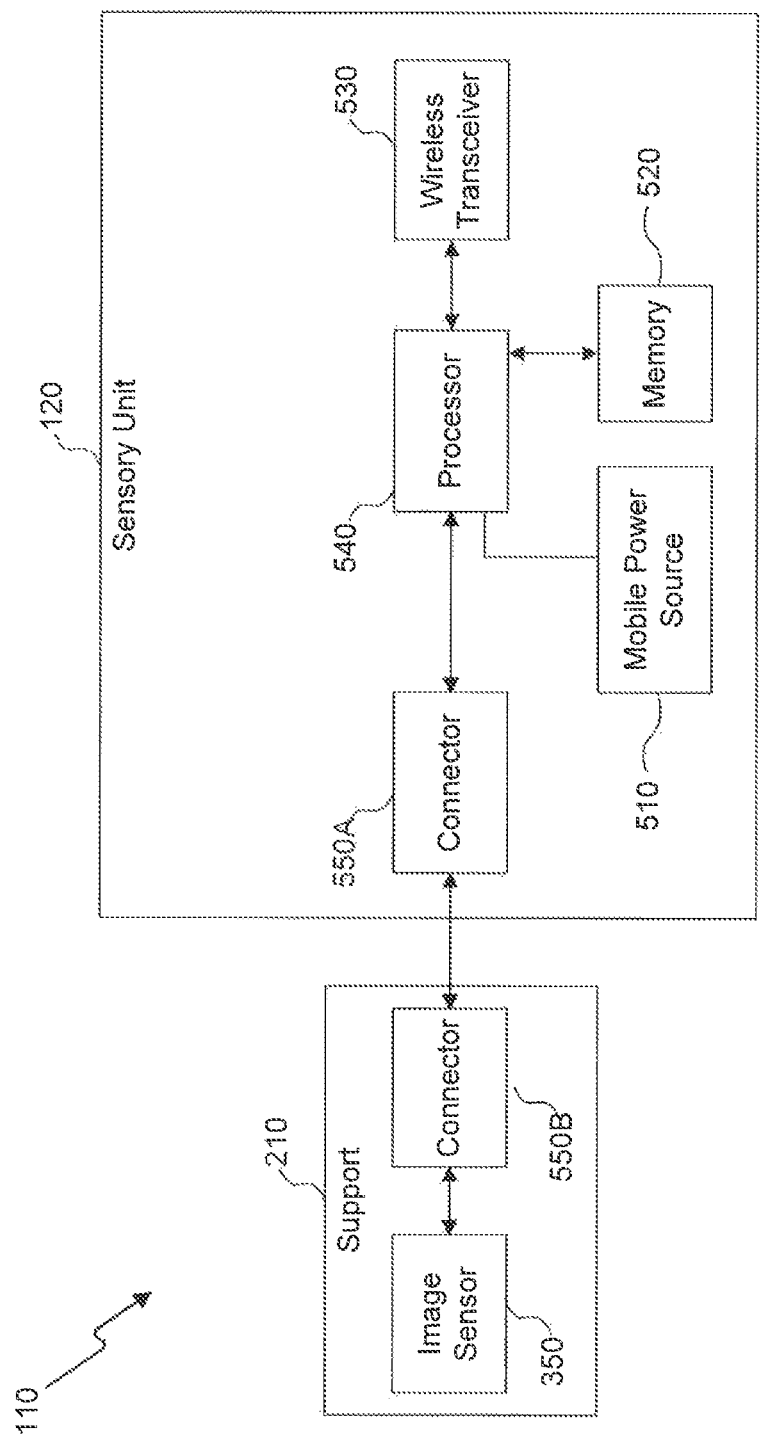
FIG. 5C is a block diagram illustrating an example of the components of an apparatus for aiding persons who have low vision according to a third embodiment.

FIG. 5C is a block diagram illustrating the components of apparatus 110 according to a third embodiment. In particular, FIG. 5C depicts an embodiment in which support 210 includes image sensor 350 and connector 550B. In this embodiment, sensory unit 120 provides functionality for processing data and, therefore, a separate processing unit is not needed in such a configuration.

As shown in FIG. 5C, sensory unit 120 includes processor 540, connector 550A, mobile power source 510, memory 520, and wireless transceiver 530. In this embodiment, apparatus 110 does not include a feedback-outputting unit. Accordingly, wireless transceiver 530 may communicate directly with a hearing aid (e.g., a Bluetooth® hearing aid). In addition, in this embodiment, image sensor 350 is included in support 210. Accordingly, when support 210 is initially mounted on glasses 105, image sensor 350 may acquire a set aiming direction. For example, a camera associated with image sensor 350 may be installed within support 210 in a predetermined angle in a position facing slightly downwards (e.g., 7-12 degrees from the horizon). Furthermore, connector 550A and connector 550B may allow data and power to be transmitted between support 210 and sensory unit 120.

Figure 5D:
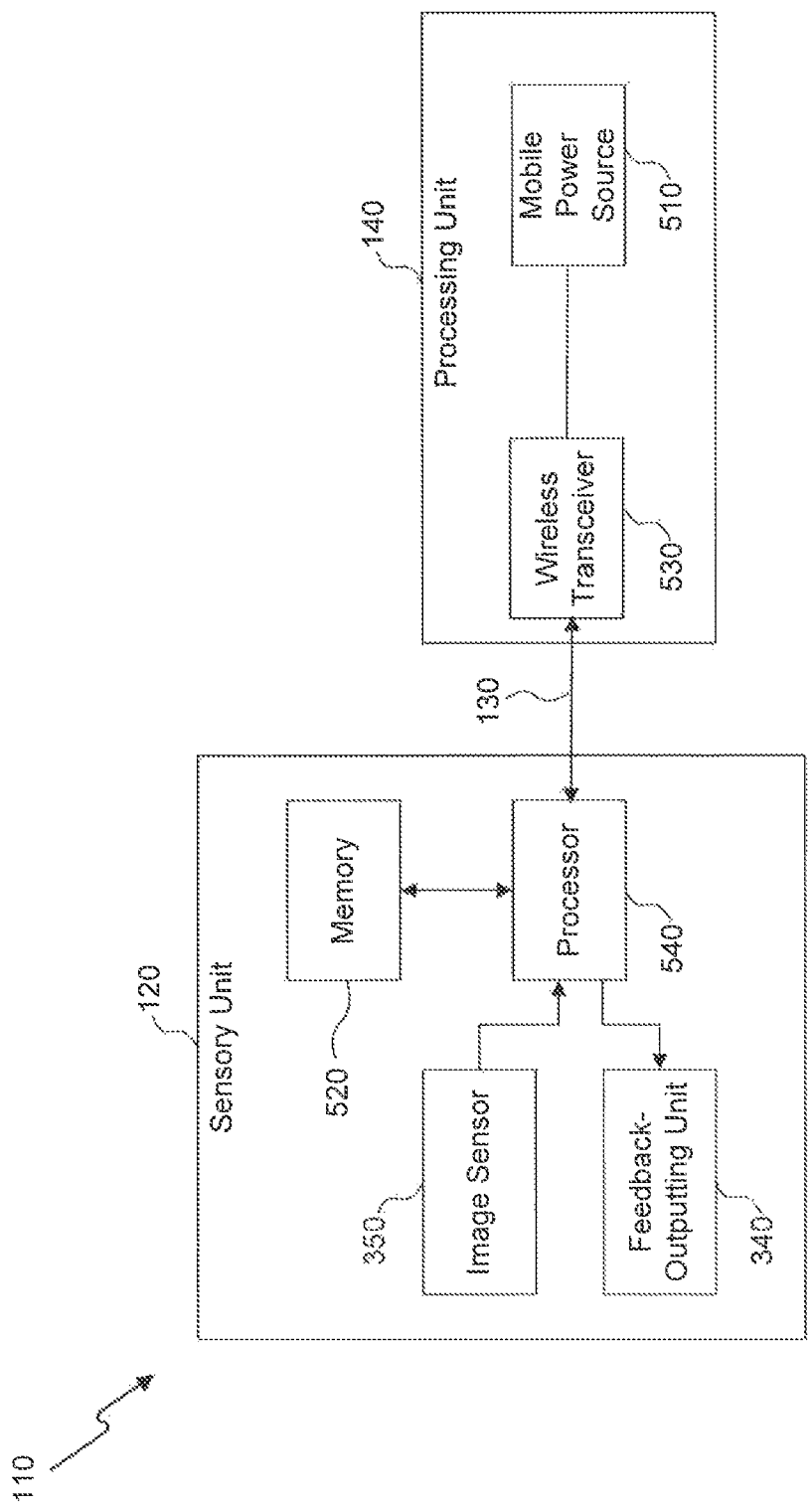
FIG. 5D is a block diagram illustrating an example of the components of an apparatus for aiding persons who have low vision according to a fourth embodiment.

FIG. 5D is a block diagram illustrating the components of apparatus 110 according to a fourth embodiment. In FIG. 5D, sensory unit 120 couples directly to a pair of glasses without the need of a support. In this embodiment, sensory unit 120 includes image sensor 350, feedback-outputting unit 340, processor 540, and memory 520. As shown in FIG. 5D, sensory unit 120 is connected via a wire 130 to processing unit 140. Additionally, in this embodiment, processing unit 140 includes mobile power source 510 and wireless transceiver 530.

As will be appreciated by a person skilled in the art having the benefit of this disclosure, numerous variations and/or modifications may be made to the disclosed embodiments. Not all components are essential for the operation of apparatus 110. Any component may be located in any appropriate part of apparatus 110 and the components may be rearranged into a variety of configurations while providing the functionality of the disclosed embodiments. Therefore, the foregoing configurations are examples and, regardless of the configurations discussed above, apparatus 110 can assist persons who have low vision with their everyday activities in numerous ways.

One way apparatus 110 can assist persons who have low vision is by identifying relevant objects in an environment. For example, in some embodiments, processor 540 may execute one or more computer algorithms and/or signal-processing techniques to find objects relevant to user 100 in image data captured by sensory unit 120. The term "object" refers to any physical object, person, text, or surroundings in an environment.

In one embodiment, apparatus 110 can perform a hierarchical object identification process. In a hierarchical object identification process, apparatus 110 can identify objects from different categories (e.g., spatial guidance, warning of risks, objects to be identified, text to be read, scene identification, and text in the wild) of image data. For example, apparatus 110 can perform a first search in the image data to identify objects from a first category, and after initiating the first search, execute a second search in the image data to identify objects from a second category.

In another embodiment, apparatus 110 can provide information associated with one or more of the objects identified in image data. For example, apparatus 110 can provide information such as the name of an individual standing in front of user 100. The information may be retrieved from a dynamic database stored in memory 520. If the database does not contain specific information associated with the object, apparatus 110 may provide user 100 with nonvisual feedback indicating that a search was made, but the requested information was not found in the database. Alternatively, apparatus 110 may use wireless transceiver 530 to search for and retrieve information associated with the object from a remote database (e.g., over a cellular network or Wi-Fi connection to the Internet).

Another way apparatus 110 can assist persons who have low vision is by performing a continuous action that relates to an object in an environment. A continuous action may involve providing continuous feedback regarding the object. For example, apparatus 110 can provide continuous feedback associated with an object identified within a field-of-view of image sensor 350, and suspend the continuous feedback when the object moves outside the field-of-view of image sensor 350. Examples of continuous feedback may include audibly reading text, playing a media file, etc. In addition, in some embodiments, apparatus 110 may provide continuous feedback to user 100 based on information derived from a discrete image or based on information derived from one or more images captured by sensory unit 120 from the environment of user 100.

Another type of continuous action includes monitoring the state of an object in an environment. For example, in one embodiment, apparatus 110 can track an object as long as the object remains substantially within the field-of-view of image sensor 350. Furthermore, before providing user 100 with feedback, apparatus 110 may determine whether the object is likely to change its state. If apparatus 110 determines that the object is unlikely to change its state, apparatus 110 may provide a first feedback to user 100. For example, if user 100 points to a road sign, apparatus 110 may provide a first feedback that comprises a descriptor of the road sign. However, if apparatus 110 determines that the object is likely to change its state, apparatus 110 may provide a second feedback to user 100 after the object has changed its state. For example, if user 100 points at a traffic light, the first feedback may comprise a descriptor of the current state of the traffic light (e.g., the traffic light is red) and the second feedback may comprise a descriptor indicating that the state of traffic light has changed (i.e., the traffic light is now green).

Apparatus 110 may also determine that an object that is expected to change its state is not functioning and provide appropriate feedback. For example, apparatus 110 may provide a descriptor indicating that a traffic light is broken.

Apparatus 110 can also assist persons who have low vision by making intelligent decisions regarding a person's intentions. Apparatus 110 can make these decisions by understanding the context of a situation. Accordingly, disclosed embodiments may retrieve contextual information from captured image data and adjust the operation of apparatus 110 based on at least the contextual information. The term "contextual information" (or "context") refers to any information having a direct or indirect relationship with an object in an environment. In some embodiments, apparatus 110 may retrieve different types of contextual information from captured image data. One type of contextual information is the time and/or the place that an image of the object was captured. Another example of a type of contextual information is the meaning of text written on the object. Other examples of types of contextual information include the identity of an object, the type of the object, the background of the object, the location of the object in the frame, the physical location of the user relative to the object, etc.

In an embodiment, the type of contextual information that is used to adjust the operation of apparatus 110 may vary based on objects identified in the image data and/or the particular user who wears apparatus 110. For example, when apparatus 110 identifies a package of cookies as an object, apparatus 110 may use the location of the package (i.e., at home or at the grocery store) to determine whether or not to read the list of ingredients aloud. Alternatively, when apparatus 110 identifies a signboard identifying arrival times for trains as an object, the location of the sign may not be relevant, but the time that the image was captured may affect the output. For example, if a train is arriving soon, apparatus 110 may read aloud the information regarding the coming train. Accordingly, apparatus 110 may provide different responses depending on contextual information.

Apparatus 110 may use contextual information to determine a processing action to execute or an image resolution of image sensor 350. For example, after identifying the existence of an object, contextual information may be used to determine if the identity of the object should be announced, if text written on the object should be audibly read, if the state of the object should be monitored, or if an image representation of the object should be saved. In some embodiments, apparatus 110 may monitor a plurality of images and obtain contextual information from specific portions of an environment. For example, motionless portions of an environment may provide background information that can be used to identify moving objects in the foreground.

Yet another way apparatus 110 can assist persons who have low vision is by automatically carrying out processing actions after identifying specific objects and/or hand gestures in the field-of-view of image sensor 350. For example, processor 540 may execute several actions after identifying one or more triggers in image data captured by apparatus 110. The term "trigger" includes any information in the image data that may cause apparatus 110 to execute an action. For example, apparatus 110 may detect as a trigger a finger of user 100 pointing to one or more coins. The detection of this gesture may cause apparatus 110 to calculate a sum of the value of the one or more coins. As another example of a trigger, an appearance of an individual wearing a specific uniform (e.g., a policeman, a fireman, a nurse) in the field-of-view of image sensor 350 may cause apparatus 110 to make an audible indication that this particular individual is nearby.

In some embodiments, the trigger identified in the image data may constitute a hand-related trigger. The term "hand-related trigger" refers to a gesture made by, for example, the user's hand, the user's finger, or any pointed object that user 100 can hold (e.g., a cane, a wand, a stick, a rod, etc.).

In other embodiments, the trigger identified in the image data may include an erratic movement of an object caused by user 100. For example, unusual movement of an object can trigger apparatus 110 to take a picture of the object. In addition, each type of trigger may be associated with a different action. For example, when user 100 points to text, apparatus 110 may audibly read the text. As another example, when user 100 erratically moves an object, apparatus 110 may audibly identify the object or store the representation of that object for later identification.

Apparatus 110 may use the same trigger to execute several actions. For example, when user 100 points to text, apparatus 110 may audibly read the text. As another example, when user 100 points to a traffic light, apparatus 110 may monitor the state of the traffic light. As yet another example, when user 100 points to a branded product, apparatus 110 may audibly identify the branded product. Furthermore, in embodiments in which the same trigger is used for executing several actions, apparatus 110 may determine which action to execute based on contextual information retrieved from the image data. In the examples above, wherein the same trigger (pointing to an object) is used, apparatus 110 may use the type of the object (text, a traffic light, a branded product) to determine which action to execute.

To assist user 100 throughout his or her daily activities, apparatus 100 may follow several procedures for saving processing resources and prolonging battery life. For example, apparatus 110 can use several image resolutions to form images. Higher image resolution provides more detailed images, but requires more processing resources. Lower image resolution provides less detailed images, but saves processing resources. Therefore, to prolong battery life, apparatus 110 may have rules for capturing and processing high resolution image under certain circumstances, and rules for capturing and processing low resolution image when possible. For example, apparatus 110 may capture higher resolution images when performing Optical Character Recognition (OCR), and capture low resolution images when searching for a trigger.

One of the common challenges persons with low vision face on a daily basis is reading. Apparatus 110 can assist persons who have low vision by audibly reading text that is present in user 100 environment. Apparatus 110 may capture an image that includes text using sensory unit 120. After capturing the image, to save resources and to process portions of the text that are relevant to user 100, apparatus 110 may initially perform a layout analysis on the text. The term "layout analysis" refers to any process of identifying regions in an image that includes text. For example, layout analysis may detect paragraphs, blocks, zones, logos, titles, captions, footnotes, etc.

In one embodiment, apparatus 110 can select which parts of the image to process, thereby saving processing resources and battery life. For example, apparatus 110 can perform a layout analysis on image data taken at a resolution of one megapixel to identify specific areas of interest within the text. Subsequently, apparatus 110 can instruct image sensor 350 to capture image data at a resolution of five megapixels to recognize the text in the identified areas. In other embodiments, the layout analysis may include initiating at least a partial OCR process on the text.

In another embodiment, apparatus 110 may detect a trigger that identifies a portion of text that is located a distance from a level break in the text. A level break in the text represents any discontinuity of the text (e.g., a beginning of a sentence, a beginning of a paragraph, a beginning of a page, etc.). Detecting this trigger may cause apparatus 110 to read the text aloud from the level break associated with the trigger. For example, user 100 can point to a specific paragraph in a newspaper and apparatus 110 may audibly read the text from the beginning of the paragraph instead of from the beginning of the page.

In addition, apparatus 110 may identify contextual information associated with text and cause the audible presentation of one portion of the text and exclude other portions of the text. For example, when pointing to a food product, apparatus 110 may audibly identify the calorie value of the food product. In other embodiments, contextual information may enable apparatus 110 to construct a specific feedback based on at least data stored in memory 520. For example, the specific feedback may assist user 100 to fill out a form (e.g., by providing user 100 audible instructions and details relevant to a form in the user's field-of-view).

To improve the audible reading capabilities of apparatus 110, processor 540 may use OCR techniques. The term "optical character recognition" includes any method executable by a processor to retrieve machine-editable text from images of text, pictures, graphics, etc. OCR techniques and other document recognition technology typically use a patter matching process to compare the parts of an image to sample characters on a pixel-by-pixel basis. This process, however, does not work well when encountering new fonts, and when the image is not sharp. Accordingly, apparatus 110 may use an OCR technique that compares a plurality of sets of image regions that are proximate to each other. Apparatus 110 may recognize characters in the image based on statistics relate to the plurality of the sets of image regions. By using the statistics of the plurality of sets of image regions, apparatus 110 can recognize small font characters defined by more than four pixels e.g., six or more pixels. In addition, apparatus 110 may use several images from different perspectives to recognize text on a curved surface. In another embodiment, apparatus 110 can identify in image data an existence of printed information associated with a system command stored in a database and execute the system command thereafter. Examples of a system command include: "enter training mode," "enter airplane mode," "backup content," "update operating system," etc.

The disclosed OCR techniques may be implemented on various devices and systems and are not limited to use with apparatus 110. For example, the disclosed OCR techniques provide accelerated machine reading of text. In one embodiment, a system is provided for audibly presenting a first part of a text from an image, while recognizing a subsequent part of the text. Accordingly, the subsequent part may be presented immediately upon completion of the presentation of the first part, resulting in a continuous audible presentation of standard text in less than two seconds after initiating OCR.

As is evident from the foregoing, apparatus 110 may provide a wide range of functionality. More specifically, one embodiment consistent with the present disclosure provides a method for informing user 100 that an object detected within the field of view of apparatus 110 is not found in one or more databases containing object information. As a result of this "failed attempt," apparatus 110 may assist the user in creating a new database entry for this new object to facilitate future rapid identification.

As used in this disclosure, a "representation" may comprise any audible or visual information associated with any object or locational setting perceived within the field of view of apparatus 110. As previously discussed, one or more such objects may be described in entries within one or more databases, which facilitate identification of the object by apparatus 110 and allow the apparatus to provide feedback to the user identifying the object.

A database may not contain information associated with each and every object or situation that a user such as user 100 may encounter in daily life. In these situations, apparatus 110 may receive image data and a signal from user 100 indicating a desire to know more about an object or situation within the image data in order to discover in rapid fashion that no information is known about the object. The ability to provide feedback on demand to the user regarding these "failed" identification attempts may be important to operation of apparatus 110. These failed attempts may provide opportunities to expand the device's capabilities, since the object can be associated with a new database entry that may be readily identified in the future. Further, the failed attempt feedback can provide confirmation to user 100 that apparatus 110 is working and operational, but simply does not have enough information to identify an object or situation.

As used in this disclosure, a "signal" from the user may include any audible input presented by user 100 to apparatus 110, or any visible activity recognizable by apparatus 110 indicating that user 100 needs help or wants information. "Information" relating to an object or a situation may include any descriptive knowledge or data associated with the entity, such as context, location, size, color, rate of motion, etc. As used herein, "feedback" generated and provided by apparatus 110 may comprise any audible, tactile, or visual information that the apparatus employs to update and inform user 100 about a particular system status, or about objects and situations perceived from the field of view of the apparatus. Apparatuses, systems, and methods for generating and providing "failed attempt" feedback will now be described in detail.

Figure 6:
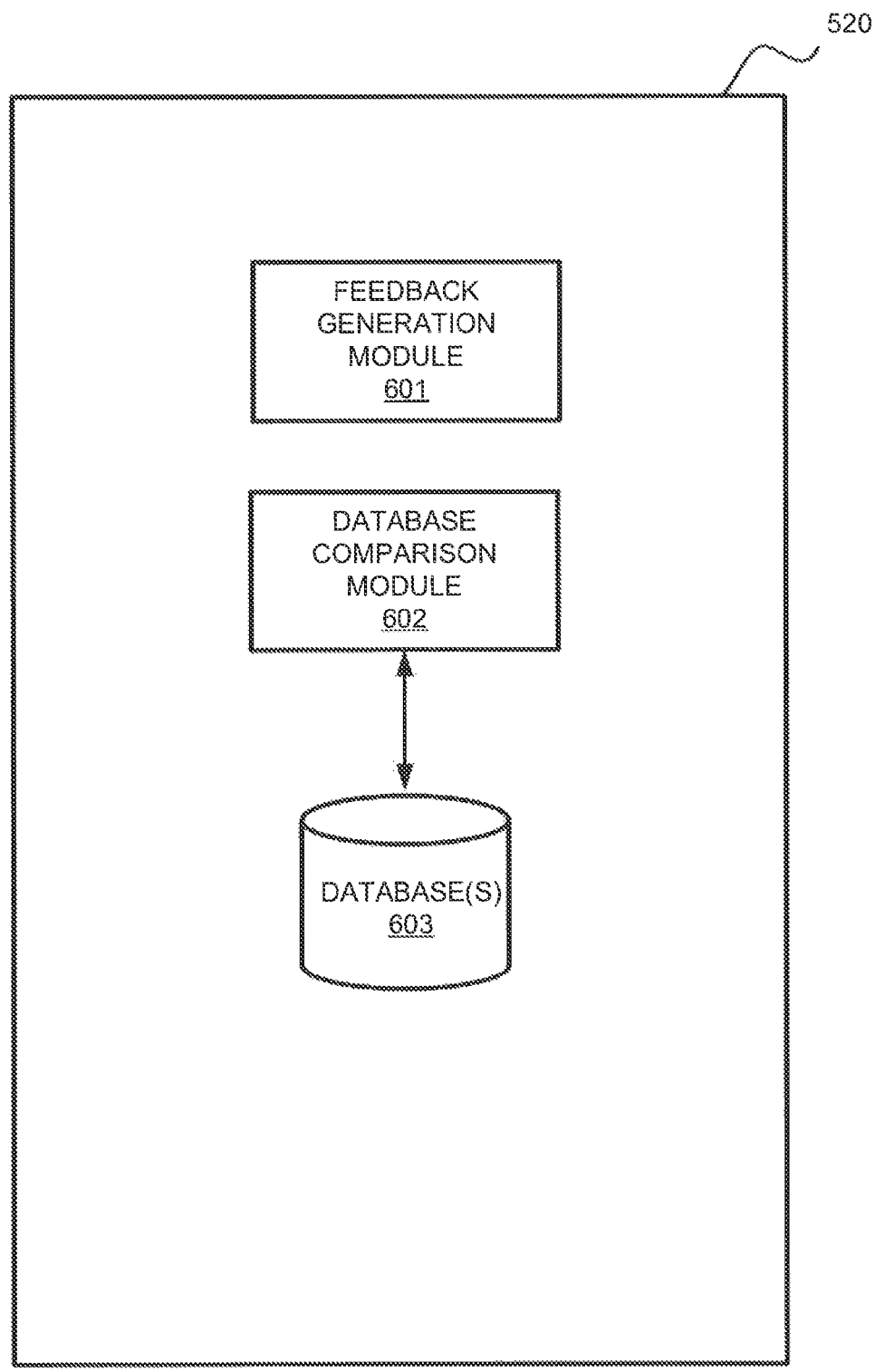
FIG. 6 is a block diagram illustrating an example of a memory contained within an apparatus for aiding persons who have low vision.

FIG. 6 is a block diagram illustrating memory 520 associated with apparatus 110 according to one embodiment. In the example shown in FIG. 6, memory 520 comprises a feedback generation module 601, a database comparison module 602, and one or more databases 603.

Feedback generation module 601 may provide functionality for apparatus 110 to generate and transmit information to user 100 in response to a query. Processor 540 may execute feedback generation module 601 to generate and process feedback in a given context, then transmit the generated feedback to feedback-outputting unit 340 for output to user 100. In one embodiment, processor 540 and feedback-outputting unit 340 may be operatively connected via wire 130. In other embodiments, processor 540 and feedback-outputting unit 340 may be operatively connected via wireless transceiver(s) 530. As discussed above, in some embodiments, feedback generation module 601 may generate audible feedback to user 100. In other embodiments, the feedback may be tactile in nature, such as a vibration.

Database comparison module 602 may provide functionality for apparatus 110 to compare objects detected in the user's environment to objects in a database, such as database 603 or remote databases 702, to be described in detail below. In some embodiments, database comparison module 602 may derive information from real time image data received from image sensor 350. In other embodiments, other software elements or processors may derive the information and provide it to database comparison module 602. Processor 540 may execute database comparison module 602 to access one or more of the described databases, and compare the information derived from the received real time image data with information in the databases. If the derived information corresponds to information found in one or more of the databases, database comparison module 602 may provide an indication to feedback generation module 601 to that effect. If the derived information is not found in any database searched by database comparison module 602, apparatus 110 will generate and provide feedback relating to the failed attempt as discussed in further detail below in association with FIGS. 8-12.

Database(s) 603 may comprise one or more databases that store information and are accessed and/or managed through memory 520. By way of example, databases 603 may include document management systems, Microsoft™ SQL databases, SharePoint™ databases, Oracle™ databases, Sybase™ databases, or other relational databases or non-relational databases, such as Hadoop sequence files, HBase, or Cassandra. The databases or other files may include, for example, data and information related to the source and destination of a network request, the data contained in the request, etc. Systems and methods of disclosed embodiments, however, are not limited to separate databases. Databases 603 may contain software code or macros that facilitate rapid searching and comparison by database comparison module 602.

Feedback generation module 601 and database comparison module 602 may be implemented in software, hardware, firmware, a mix of any of those, or the like. For example, if feedback generation module 601 and database comparison module 602 are implemented in software, they may be stored in memory 520, as shown in FIG. 6. Other components of processing unit 140 and/or sensory unit 120 may be configured to perform processes to implement and facilitate operations of identification module 610 and feedback module 620. Thus, feedback generation module 601 and database comparison module 602 may include software, hardware, or firmware instructions (or a combination thereof) executable by one or more processors (e.g., processor 540), alone or in various combinations with each other. For example, feedback generation module 601 and database comparison module 602 may be configured to interact with each other and/or other modules of apparatus 110 to perform functions consistent with disclosed embodiments. In some embodiments, any of the disclosed modules (e.g., feedback generation module 601 and database comparison module 602) may each include dedicated sensors (e.g., IR, image sensors, etc.) and/or dedicated application processing devices to perform the functionality associated with each module.

Figure 7:
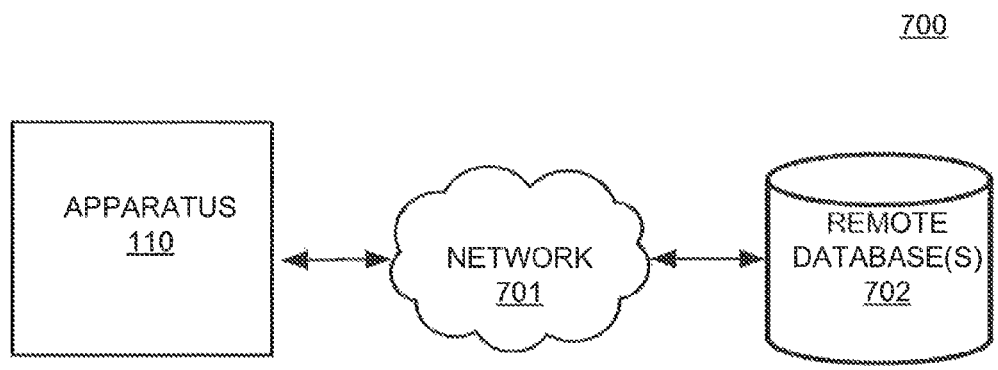
FIG. 7 is a block diagram illustrating an example of a system environment for aiding persons who have low vision.

FIG. 7 is an example illustration of a system 700 for providing feedback to a visually-impaired user, consistent with a disclosed embodiment. As shown in system 700, apparatus 110 and remote database(s) 702 are configured to communicate over a network 701. One of skill in the art will appreciate that although one apparatus and one remote database are depicted in FIG. 7, any number of these components may be provided. Furthermore, one of ordinary skill in the art will recognize that one or more components of system 700 may be combined and/or divided into subcomponents.

Network 701 provides communications between the various components in system 700, such as apparatus 110 and remote database(s) 702. In addition, the components in system 700 may access legacy systems (not shown) via network 701, or may directly access legacy systems, data stores, or other network applications. Network 701 may be a shared, public, or private network, may encompass a wide area or local area, and may be implemented through any suitable combination of wired and/or wireless communication networks. Network 701 may further comprise an intranet or the Internet.

Apparatus 110 may comprise any configuration of the apparatus illustrated in FIGS. 5A-5D. Apparatus 110 may configure wireless transceiver 530 to communicate with other components of system 700 via network 701, or may contain other components (not shown) which facilitate network communication.

Remote database(s) 702 may, as described above in relation to databases 603, comprise one or more databases that store information and are accessible by apparatus 110 via network 701. Databases 702 may contain or be linked to components (not shown) that facilitate communication over network 701. By way of example, databases 702 may be document management systems, Microsoft™ SQL databases, SharePoint™ databases, Oracle™ databases, Sybase™ databases, or other relational databases or non-relational databases, such as Hadoop sequence files, HBase, or Cassandra. The databases or other files may include, for example, data and information related to the source and destination of a network request, the data contained in the request, etc. Systems and methods of disclosed embodiments, however, are not limited to separate databases. Databases 702 may contain software code or macros that facilitate rapid searching and comparison by database comparison module 602 of apparatus 110.

Figure 8:
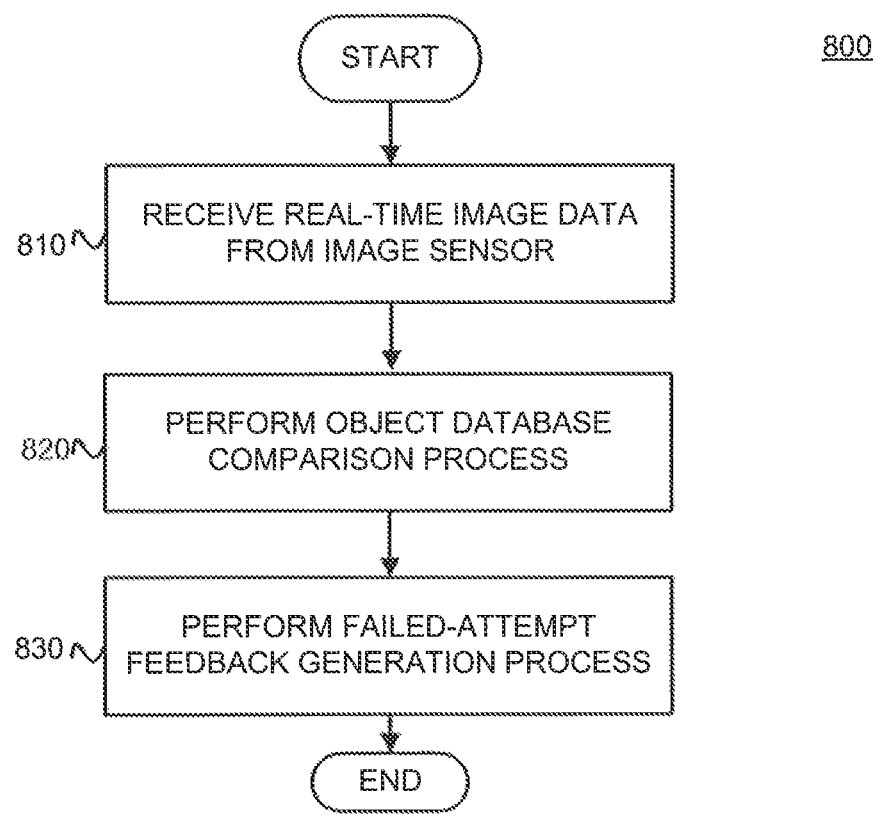
FIG. 8 is an example of a process for providing feedback to a person who has low vision, consistent with disclosed embodiments.

FIG. 8 illustrates an example process 800 for providing feedback to a person who has low vision consistent with certain disclosed embodiments. Process 800, as well as any or all of the individual steps therein, may be performed by various aspects of device 110, such as sensory unit 120, processing unit 140, support 210, or any subcomponents therein. For exemplary purposes, FIG. 8 is described as being performed by processor 540, executing software instructions stored within memory 520.

Processor 540 may receive real-time image data from an image sensor, such as image sensor 350 (Step 810). In other embodiments, processor 540 may receive the image data from an intermediate component associated with sensory unit 120. The intermediate unit may, for example, perform image processing operations on the real-time image data before transmitting it to processor 540. In some embodiments, the real-time image data may be received as a single streaming video file. In other embodiments, the real-time image data may be received as a series of still images. When the image data is received, processor 540 may store the data in memory 520 or databases 603.

Processor 540, via database comparison module 602, may perform an object database comparison process, such as is described below in connection with FIG. 9 (Step 820). In brief, according to some embodiments, database comparison module 602 may select one or more databases, such as databases 603 or remote databases 702 to search for information relating to the objects in the received real-time image data associated with the user request. Database comparison module 602 may then access the selected databases. As discussed previously, processor 540 may determine trigger information, either audio or visual, from the received real-time image data. Processor 540 may further determine context information from the real-time image data. Finally, database comparison module 602 may perform an object database query process, such as is described below in connection with FIG. 10.

In Step 830 of process 800, processor 540, via feedback generation module 601, may perform a failed-attempt feedback generation process, such as is described below in connection with FIG. 11. In brief, according to some embodiments, feedback generation module 601 may configure the content of feedback to provide to user 100 when database comparison module 602 determines that the object(s) identified in the real-time image data are not contained within databases 603 or remote databases 702. Feedback generation module 601 may generate this "failed-attempt feedback," then provide it to user 100. Processor 540 may determine if user 100 wishes to add the representation of the object and an audible representation of the object to one or more of databases 603 or remote databases 702. If so, database comparison module 602 may perform a database entry addition process, such as is described below in connection with FIG. 12.

Figure 9:
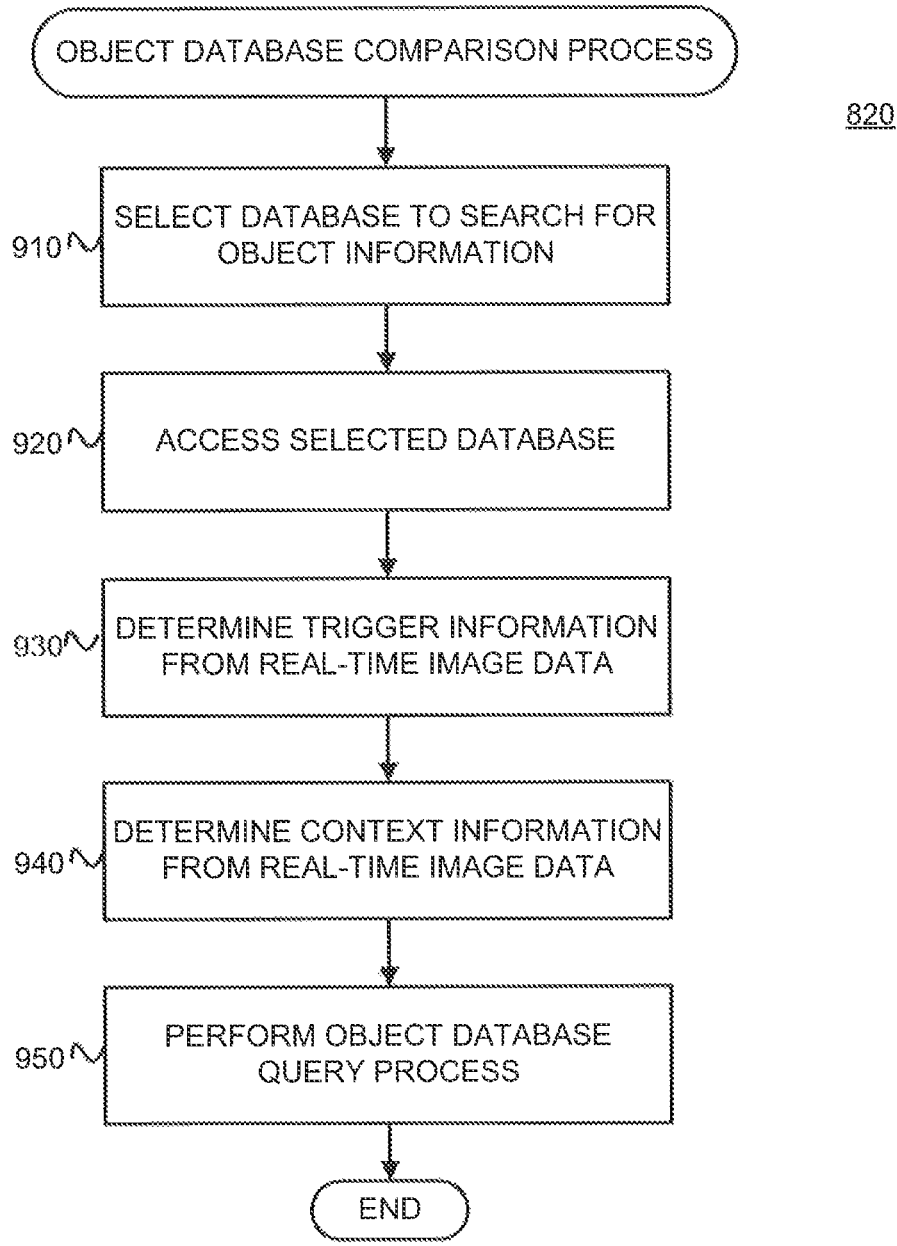
FIG. 9 is an example of an object database comparison process, consistent with disclosed embodiments.

FIG. 9 illustrates an example object database comparison process such as that described above in association with Step 820 of process 800 consistent with certain disclosed embodiments. Process 820, as well as any or all of the individual steps therein, may be performed by various aspects of device 110, such as sensory unit 120, processing unit 140, support 210, or any subcomponents therein. For exemplary purposes, FIG. 9 is described as being performed by processor 540, executing software instructions stored within memory 520.

Processor 540, via database comparison module 602, may select one or more databases to search for object information (Step 910). The database may be a mobile database contained within apparatus 110, such as database(s) 603 housed within memory 520. In other embodiments, the database may be one or more remote databases accessible over a network, such as remote database(s) 702 accessible over network 701. Once the target database(s) are selected, processor 540 may access the selected database(s) (Step 920). In some embodiments, processor 540 may provide credentials that permit its access to the database, particularly for remote database(s) 702 located on an external server.

Processor 540 may determine trigger information from the received real-time image data (Step 930). As part of the determination, processor 540 may receive a request for object information from user 100 relating to one or more representations of objects in the environment of the user contained within the received real-time image data. In some embodiments, the trigger information may comprise audible cues received from a microphone (not shown) associated with apparatus 110. In other embodiments, the trigger information may comprise one or more visual signals performed by user 100 within the received real-time image data, such as a hand signal or other such trigger. In still other embodiments, processor 540 may be configured to determine a head movement of user 100, and use the head movement as the signal indicating the desire of the user to obtain information about a given object within the field of view of apparatus 110. It is understood that these are non-limiting examples, and that apparatus 110 may receive a request for object information via any manner of trigger information.

Processor 540 may determine context information from the received real-time image data that facilitates the retrieval of information (Step 940). In some embodiments, processor 540 may execute software instructions to process the representations of the one or more objects in the real-time image data associated with the detected trigger information described above. In some embodiments, the processing may comprise image processing, such as image rotation, a change in the size of the image, image sharpening, cropping the image, enhancing the focus, etc. It is understood that these are non-limiting examples and that any manner of image processing may be applied to the real-time image data. In other embodiments, the processing may comprise optical character recognition (OCR), when the real-time image data comprises text. In these embodiments, the optical character recognition may facilitate recognition of the visualized text by processor 540, and facilitate formation of a search query for a database containing object information. Processor 540 may further derive or determine any other information contained in the received real-time image data relating to the context of the image, such as date, time, geographical location, etc.

In Step 950, processor 540, via database comparison module 602, may perform an object database query process, such as is described below in connection with FIG. 10. In brief, according to some embodiments, database comparison module 602 may query one or more selected databases (such as database(s) 603 or remote database(s) 702) using information such as the determined trigger information and context information. Database comparison module 602 may determine if an existing trigger and context matched set entry within the databases corresponds to the system status observed in the real-time image data. If so, processor 540, via feedback generation module 601, may prepare audible or tactile feedback to user 100 identifying the object. If no existing trigger and context entry matches the current system status, database comparison module 602 may determine whether or not there are further database entries to search, and may continue to compare trigger information and context information with the entries in the databases until they are exhausted. If the database entries are exhausted without matching the current system status, processor 540 may prepare "failed-attempt" feedback via feedback generation module 601.

Figure 10:
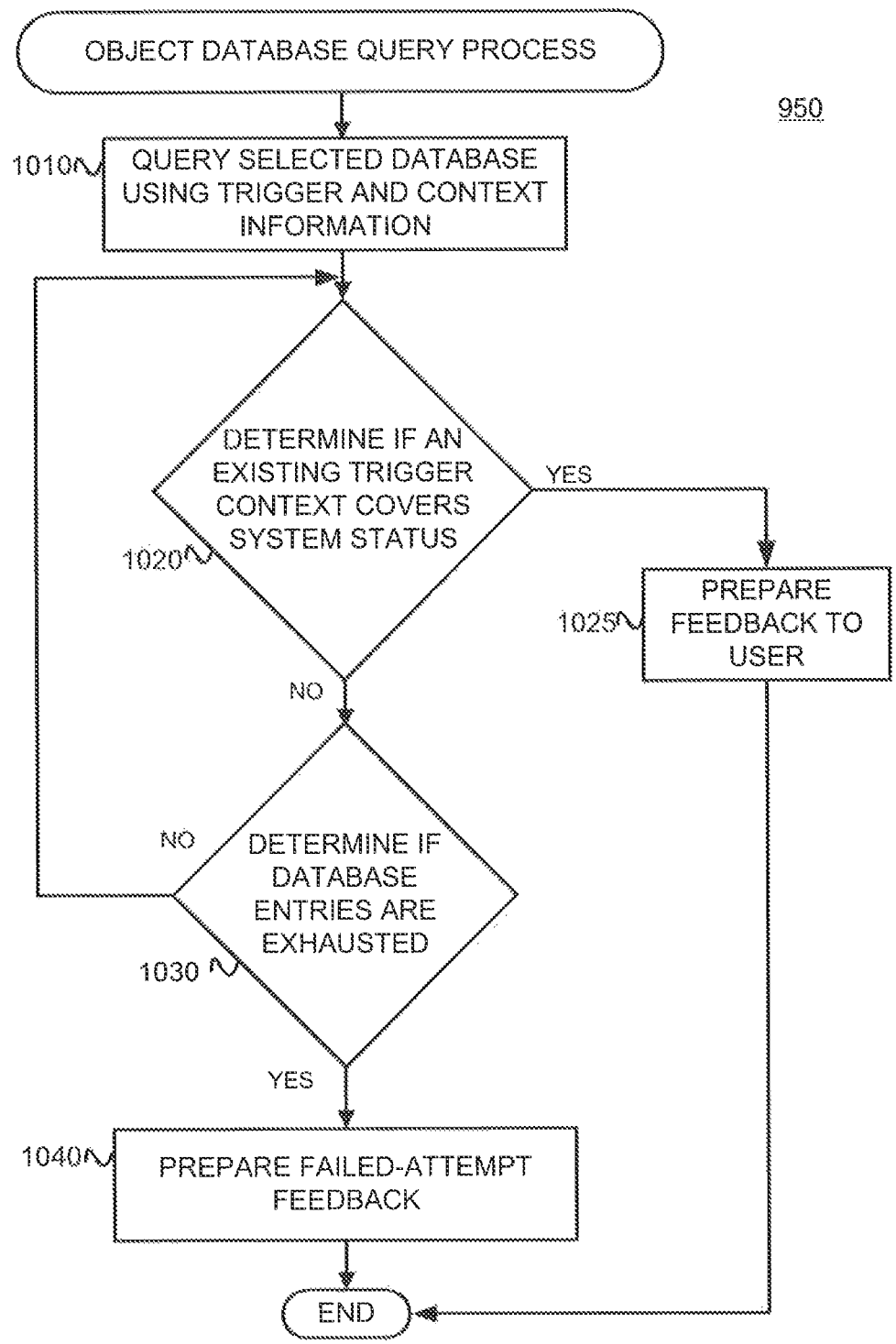
FIG. 10 is an example of an object database query process, consistent with disclosed embodiments.

FIG. 10 illustrates an example object database query process such as that described above in association with Step 950 of process 820 consistent with certain disclosed embodiments. Process 950, as well as any or all of the individual steps therein, may be performed by various aspects of device 110, such as sensory unit 120, processing unit 140, support 210, or any subcomponents therein. For exemplary purposes, FIG. 10 is described as being performed by processor 540, executing software instructions stored within memory 520.

Processor 540, via database comparison module 602, may query the selected databases, such as database(s) 603 and/or remote database(s) 702 (Step 1010). Database comparison module 602 may form a query using trigger information or context information derived from the real-time image data, or a combination of the two. In some embodiments, additional audible or visual information may form a portion of the query, if the databases are configured to contain such information and if such information was derived from the image data by processor 540.

Database comparison module 602 may determine if an existing database entry comprises trigger information and/or context information that covers or matches the current system status and the received real-time image data (Step 1020). If the status does match an existing entry (Step 1020:YES), then processor 540 may prepare feedback to user 100 identifying the object via feedback generation module 601, and the process terminates (Step 1025).

Alternatively, if no database entry matches the present system status (Step 1020: NO), then database comparison module 602 may determine if the database entries are exhausted, or if there are more entries to search (Step 1030). In alternative embodiments, database comparison module 602 may also choose a different database to query at this stage with the same search query. In other embodiments, database comparison module 602 may alter the search query. If there are more database entries to search, or if the database and/or query are otherwise modified (Step 1030:NO), then database comparison module 602 repeats Steps 1020-1030 and continues to compare the search query with existing database entries.

If database comparison module 602 determines that the database entries are exhausted (Step 1030: YES), then the comparison process ends. In some embodiments, the database comparison process may end due to other input, such as an expiration of a certain amount of time as measured by a timer associated with processor 540 (not shown). In other alternative embodiments, user 100 may provide input to apparatus 110 that halts the comparison process. After the database query comparison ends, processor 540 may begin to prepare feedback informing user 100 of the failed attempt and lack of object identification (Step 1040).

Figure 11:
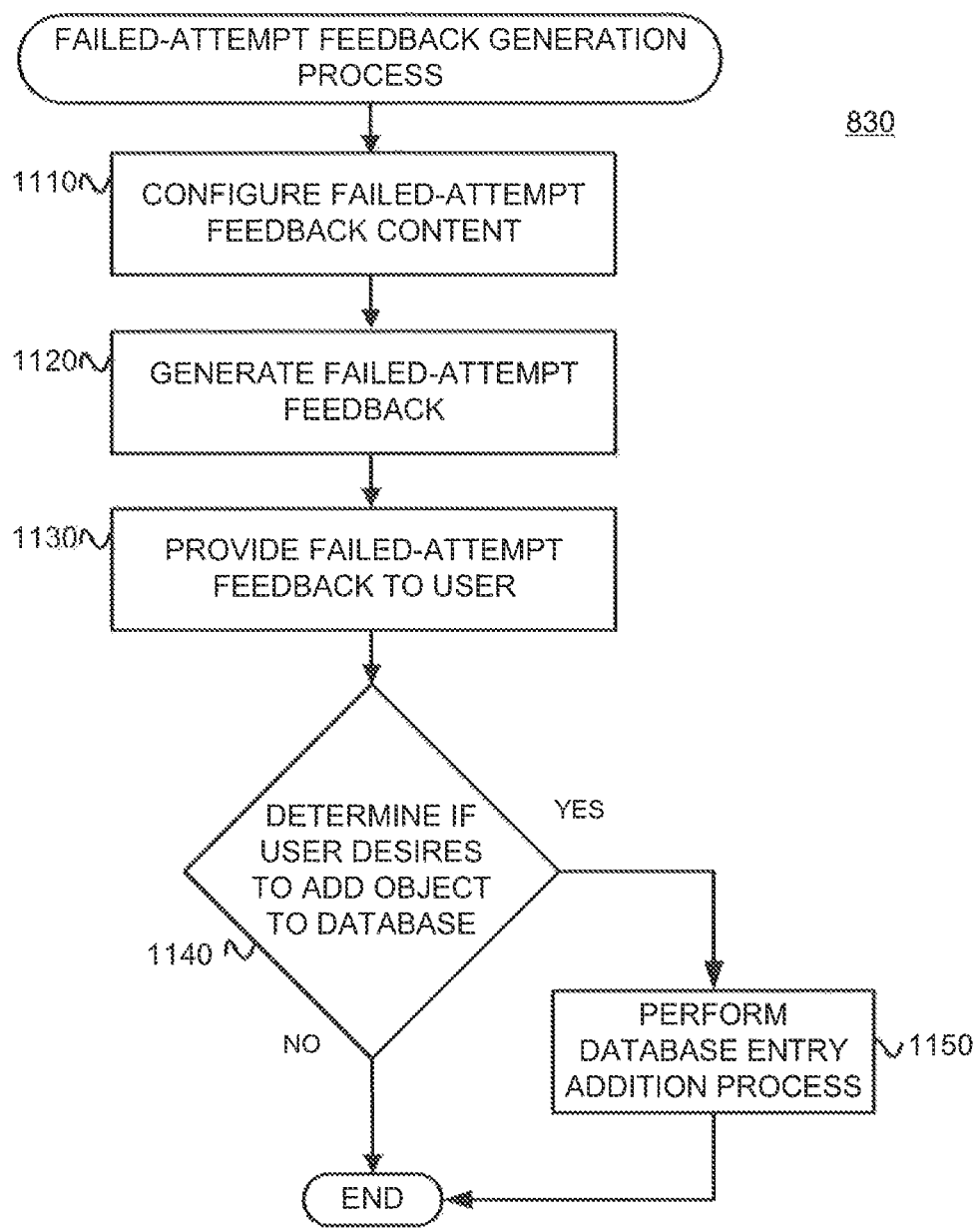
FIG. 11 is an example of a failed-attempt feedback generation process, consistent with disclosed embodiments.

FIG. 11 illustrates an example failed-attempt feedback generation process such as that described above in association with Step 830 of process 800 consistent with certain disclosed embodiments. Process 830, as well as any or all of the individual steps therein, may be performed by various aspects of apparatus 110, such as sensory unit 120, processing unit 140, support 210, or any subcomponents therein. For exemplary purposes, FIG. 11 is described as being performed by processor 540, executing software instructions stored within memory 520.

Processor 540, via feedback generation module 601, may configure the content of the failed-attempt feedback (Step 1110). As discussed previously, the feedback may be in an audible form. In these embodiments, apparatus 110 may provide user 100 with audible feedback such as "SORRY; OBJECT NOT FOUND," or "NEW OBJECT DETECTED." In other embodiments, the feedback may be in a tactile form. For example, apparatus 110 may contain components that generate vibration, and these components may be configured to vibrate in a particular pattern signifying to user 100 when an object is not found in the database. It is understood that these are merely non-limiting examples, and that feedback generation module 601 may configure any content for the feedback that may be relevant to the instant situation or context.

Once feedback generation module 601 determines and configures the content of the failed-attempt feedback, feedback generation module 601 may generate the feedback and transmit it to other components of apparatus 110 (Step 1120). In some embodiments, feedback generation module 601 may access a pre-configured feedback file matching the determined content. A feedback file may comprise a set of software instructions stored in one or more of memory 520, database(s) 603, or remote database(s) 702 that contains software instructions encoding audible feedback that may be read and outputted by feedback generation module 601 and feedback-outputting unit 430. In other embodiments, feedback generation module 601 may generate a new feedback file. In these embodiments, the new feedback file may be stored for further use in one or more of memory 520, database(s) 603, or remote database(s) 702 via network 701. Once the feedback file (whether audible, tactile, visual, or a combination thereof) is generated, feedback generation module 601 may transfer or transmit the file to other components of apparatus 110 for output to user 100, such as feedback-outputting unit 340 and/or wireless transceiver 530. These components may then provide the failed-attempt feedback to user 100 (Step 1130).

In some embodiments, processor 540 may be configured to add new entries to one or more of database(s) 603 or remote database(s) 702. In these embodiments, after providing the nonvisual failed-attempt feedback to user 100, processor 540 may determine if user 100 desires to add a representation of the object to one or more accessible databases described above (Step 1140). If user 100 does not wish to add the object to the database, or if for some other reason apparatus 110 is not configured to do so (Step 1140: NO), then the process terminates. If user 100 does wish to add a representation of the "failed" object to the database (Step 1140: YES), then database comparison module 602 may perform a database entry addition process (Step 1150), which will now be described in detail.

Figure 12:
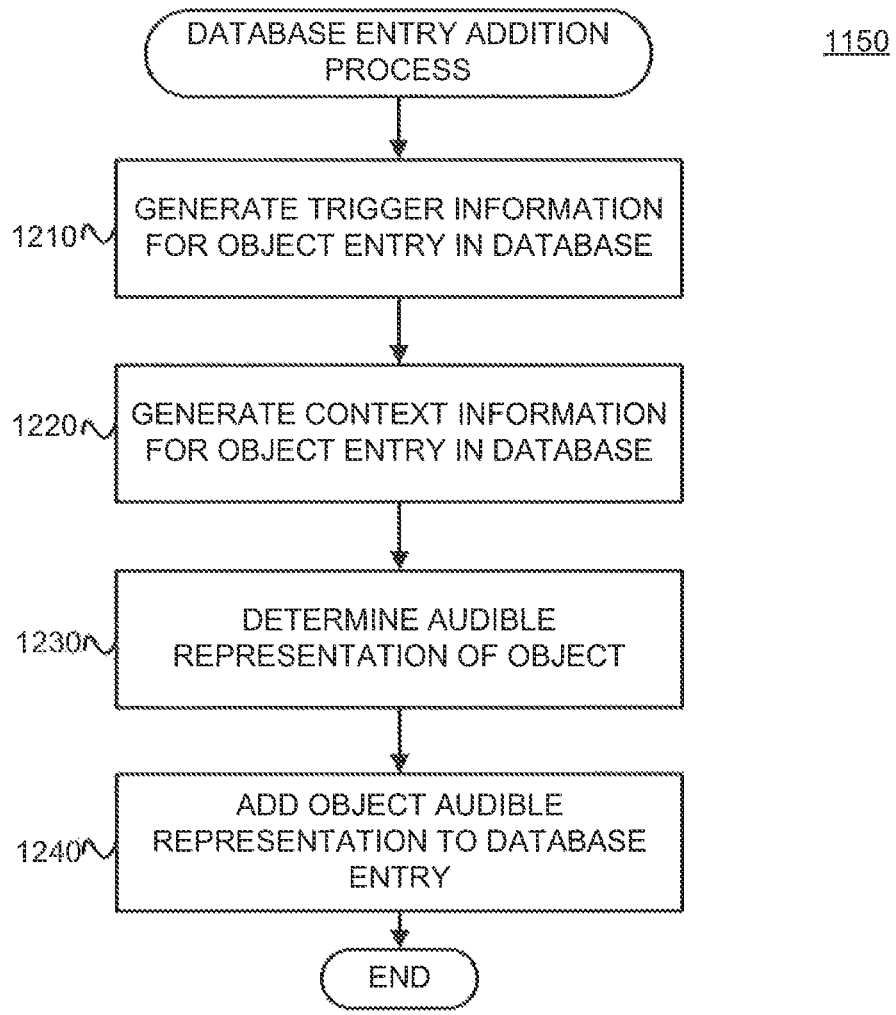
FIG. 12 is an example of a database entry addition process, consistent with disclosed embodiments.

FIG. 12 illustrates an example database entry addition process such as that described above in association with Step 1150 of process 830 consistent with certain disclosed embodiments. Process 1150, as well as any or all of the individual steps therein, may be performed by various aspects of device 110, such as sensory unit 120, processing unit 140, support 210, or any subcomponents therein. For exemplary purposes, FIG. 12 is described as being performed by processor 540, executing software instructions stored within memory 520.

Processor 540, via database comparison module 602, may generate trigger information to be associated with the new object in one or more of database(s) 603 and remote database(s) 702 (Step 1210). Database comparison module 602 may use information derived previously from the real-time image data as discussed above, or may analyze a stored representation of the object anew. The trigger information may comprise a gesture, action, or other input that may invoke actions associated with the newly-identified object in the future. For example, if the new object is a bus (or other such motor vehicle), the trigger may comprise pointing at the object. Any trigger contemplated by one skilled in the art may be used that would be detectable by the components of apparatus 110.

Database comparison module 602 may further generate context information to be associated with the database entry for the new object (Step 1220). Context information may comprise any information related to the object or the setting that facilitates unique identification. In some embodiments, the context information may comprise a geographical location based on GPS coordinates. For example, if the "new" object is a bus, as in the example above, context information relating to the bus may comprise the street on which the bus was seen, or the location of a bus stop where the bus had paused to gather passengers. In other embodiments, context information may comprise information relating to the date and time when the object was seen. Continuing the bus example, additional context information may include that the bus was at a particular bus stop on a particular day at a particular time of day. In other embodiments, context information may include additional information about the object itself. In the bus example, this might include the color of the bus. In these embodiments, context might further include text that was recognized via OCR as described above. The text may include the name of the organization associated with the bus, or identifying route information. Therefore, an example of a full picture of the context information for a given object, such as a bus, might include "Orange bus, Route 6, at the bus stop at Freedom Drive and Explorer Street at 4:00 PM on Thursdays. Route is the Northern Line going to the Airport." Any such contextual information may be determined by processor 540 and associated with the object in database(s) 603 or remote database(s) 702.

In some embodiments, processor 540, via feedback generation module 601 and/or database comparison module 602, may determine an audible representation of the object to further complete the object's database entry (Step 1230). Carrying forward the example above, an example audible representation for the given situation might be "THIS IS A NORTHERN LINE ROUTE 6 BUS GOING TO THE AIRPORT." Feedback generation module 601 may generate the content of the audible representation, in conjunction with feedback-outputting unit 340, and may add the audible representation of the object to its database entry (Step 1240). A particular object may have more than one audible representation associated with it. For example, if multiple triggers or multiple contexts are associated with the object, each of the triggers and/or contexts may be associated with its own audible representation. Feedback generation module 601 may individually generate each of the necessary representations and associate them with the entry in the database.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks, floppy disks, or CD ROM, or other forms of RAM or ROM, USB media, DVD, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, C++, Objective-C, HTML, HTML/AJAX combinations, XML, or HTML with included Java applets. One or more of such software sections or modules can be integrated into a computer system or existing e-mail or browser software.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed routines may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. An apparatus for providing feedback to a visually impaired user, the apparatus comprising:
    a mobile image sensor configured to capture real time image data from an environment of the user;
    a mobile power source for powering at least the image sensor;
    at least one mobile processor device configured to:
        receive from the mobile image sensor real time image data that includes a representation of a physical object in the environment of the user;
        identify a hand-related trigger in the real time image data, wherein the hand-related trigger is associated with a desire of the user to obtain information about the physical object;
        based on at least the identification of the hand-related trigger, access a database holding information about a plurality of objects;
        compare information derived from the received real time image data with information in the database; and
        provide the user with nonvisual feedback indicating that the information about the physical object is not locatable in the database.

2. The apparatus of claim 1, wherein the image sensor is further configured to be connected to glasses worn by the visually impaired user, and is thereby configured to be movable with a head of the visually impaired user.

3. The apparatus of claim 1, wherein the image sensor is further configured to be movable with a head of the visually impaired user and an aiming direction of the image sensor substantially coincides with a field of view of the visually impaired user.

4. The apparatus of claim 1, wherein the mobile power source is rechargeable and contained within a housing that holds the at least one mobile processor device.

5. The apparatus of claim 1, wherein the at least one mobile processor device is further configured to determine a head movement of the visually impaired user and to use the head movement as the signal indicating the desire of the user to obtain information about the physical object.

6. The apparatus of claim 1, wherein the physical object in the environment of the user is a face of an individual.

7. The apparatus of claim 1, wherein the physical object in the environment of the user is an inanimate object.

8. The apparatus of claim 1, wherein the physical object in the environment of the user is merchandise.

9. The apparatus of claim 1, wherein the at least one mobile processor device is further configured to access a mobile database contained within a housing that holds the mobile power source.

10. The apparatus of claim 1, wherein the at least one mobile processor device is further configured to access a remote database associated with a server having an Internet connection.

11. The apparatus of claim 1, wherein the at least one mobile processor device is further configured to compare the representation of the physical object with the information in the database.

12. The apparatus of claim 1, wherein the nonvisual feedback includes an audible tone.

13. The apparatus of claim 1, wherein the nonvisual feedback includes a tactile response.

14. The apparatus of claim 1, wherein the at least one mobile processor device is further configured to add the representation of the physical object and an audible representation of the physical object to the database, after providing the nonvisual feedback.

15. An apparatus for providing feedback to a user, the apparatus comprising:
   a mobile image sensor configured to be connected to glasses worn by the user to capture real time image data that substantially coincides with a field of view of the user;
   a mobile power source for powering at least the image sensor;
   at least one mobile processor device configured to:
      receive from the mobile image sensor real time image data that includes a representation of a physical object in an environment of the user;
      identify a hand-related trigger in the image data, wherein the hand-related trigger is associated with a desire of the user to obtain information about the physical object;
      based on at least the identification of the hand-related trigger, process the representation of the physical object to attempt to retrieve information; and
      provide the user with nonvisual feedback indicating that the information about the physical object was not retrieved.

16. The apparatus of claim 15, wherein processing the representation of the physical object includes performing image processing.

17. The apparatus of claim 15, wherein processing the representation of the physical object includes accessing a database holding information about a plurality of objects and comparing the representation of the physical object with information in the database.

18. The apparatus of claim 17, wherein the database includes a mobile database contained within a housing that holds the mobile power source.

19. The apparatus of claim 17, wherein the database includes a remote database associated with a server having an Internet connection.

20. The apparatus of claim 15, wherein the at least one mobile processor device is further configured to add an identifier of the physical object and an audible representation of the physical object to the database, after providing the nonvisual feedback.

21. The apparatus of claim 15, wherein the physical object is at least one of: a face, inanimate object, and merchandise.

22. A method for providing feedback to a visually impaired user, the method comprising:
   receiving from a mobile image sensor real time image data that includes a representation of a physical object in an environment of the visually impaired user, wherein the mobile image sensor is configured to be connected to glasses worn by the visually impaired user;
   identifying a hand-related trigger in the real time image data, wherein the hand-related trigger is associated with a desire of the user to obtain information about the physical object;
   based on at least the identification of the hand-related trigger, accessing a database holding information about a plurality of objects;
   comparing information derived from the received real time image data with information in the database; and
   providing the visually impaired user with nonvisual feedback that the physical object is not locatable in the database.

23. A software product stored on a non-transitory computer readable medium and comprising data and computer implementable instructions for carrying out the method of claim 22.

* * * * *